United States Patent
Nazarian et al.

(10) Patent No.: US 12,416,418 B2
(45) Date of Patent: Sep. 16, 2025

(54) PORTABLE TEMPERATURE CONTROLLED DEVICE

(71) Applicant: Therabody, Inc., Los Angeles, CA (US)

(72) Inventors: Benjamin Nazarian, Los Angeles, CA (US); Jaime Sanchez Solana, Los Angeles, CA (US); Washington Alexander Silva Garces, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/425,382

(22) Filed: Jan. 29, 2024

(65) Prior Publication Data

US 2025/0043965 A1 Feb. 6, 2025

Related U.S. Application Data

(63) Continuation of application No. 18/362,349, filed on Jul. 31, 2023.

(51) Int. Cl.
| | | |
|---|---|---|
| *F24F 1/04* | (2011.01) | |
| *F24F 5/00* | (2006.01) | |
| *F24F 11/63* | (2018.01) | |

(52) U.S. Cl.
CPC ............. *F24F 1/04* (2013.01); *F24F 5/0042* (2013.01); *F24F 11/63* (2018.01)

(58) Field of Classification Search
CPC . F24F 1/04; F24F 11/63; F24F 5/0042; A61F 2007/0075; F25B 21/02;

(Continued)

(56) References Cited

U.S. PATENT DOCUMENTS

| 1,545,027 | A | 7/1925 | Ashlock |
|---|---|---|---|
| D143,678 | S | 1/1946 | L. et al. |

(Continued)

FOREIGN PATENT DOCUMENTS

| CA | 178767 S | 9/2018 |
|---|---|---|
| CN | 201239336 Y | 5/2009 |

(Continued)

OTHER PUBLICATIONS alexnld.com: "Adjustable Waist Support Belt 3 Modes Heating Back Massage Band Lumbar Brace," Available at least as early as Dec. 6, 2021, 18 Pages, Retrieved from URL: https://alexnld.com/product/adjustable-waist-support-belt-3-modes-heating-back-massage-band-lumbar-brace/.

(Continued)

*Primary Examiner* — Nelson J Nieves
(74) *Attorney, Agent, or Firm* — Sterne, Kessler, Goldstein & Fox P.L.L.C.

(57) ABSTRACT

A portable temperature-controlled device includes a housing and a controllable temperature element having a first surface and a second surface, wherein the first surface opposes the second surface. Inside the housing, a heat sink is disposed and in contact with the first surface of the controllable temperature element, and a fan is disposed adjacent the heat sink inside the housing and configured to direct heat away from the heat sink. The portable temperature-controlled device further includes a heat spreader in contact with the controllable temperature element for thermal energy transfer. The heat sink and the fan are supported on a support member inside the housing.

16 Claims, 23 Drawing Sheets

(58) Field of Classification Search
CPC ........ F25D 31/007; F25D 11/003; F25D 3/08; F25D 2400/12; F25D 29/003; F25D 2331/805; F25D 2331/803
See application file for complete search history.

(56) References Cited

U.S. PATENT DOCUMENTS

| | | | |
|---|---|---|---|
| 2,987,334 A | 6/1961 | Wendling | |
| 3,705,579 A | 12/1972 | Morini et al. | |
| D230,522 S | 2/1974 | Norman | |
| 3,971,229 A * | 7/1976 | Privas | A61F 7/00 62/3.62 |
| 4,046,142 A | 9/1977 | Whitney | |
| D265,002 S | 6/1982 | Hubner | |
| 4,976,706 A | 12/1990 | Aki et al. | |
| 5,014,681 A | 5/1991 | Heeman et al. | |
| 5,092,317 A | 3/1992 | Zelikovski | |
| 5,103,809 A | 4/1992 | DeLuca et al. | |
| D353,205 S | 12/1994 | Canavan | |
| D417,284 S | 11/1999 | Kondo | |
| 6,093,164 A | 7/2000 | Davis et al. | |
| D439,984 S | 4/2001 | Thach | |
| 6,406,445 B1 | 6/2002 | Ben-Nun | |
| 6,558,338 B1 | 5/2003 | Wasserman | |
| 6,567,696 B2 * | 5/2003 | Voznesensky | A61N 1/36021 607/108 |
| 6,591,142 B1 | 7/2003 | Dea | |
| D479,877 S | 9/2003 | Lee et al. | |
| 6,823,762 B2 | 11/2004 | Hu | |
| 6,846,295 B1 | 1/2005 | Ben-Nun | |
| D518,895 S | 4/2006 | Weaver, II et al. | |
| 7,022,093 B2 | 4/2006 | Smith et al. | |
| 7,207,953 B1 | 4/2007 | Goicaj | |
| D554,268 S | 10/2007 | Harding | |
| D554,761 S | 11/2007 | Marin | |
| D571,923 S | 6/2008 | Roberts | |
| 7,431,706 B2 | 10/2008 | Louis | |
| D582,047 S | 12/2008 | Yim | |
| 7,509,692 B2 | 3/2009 | Elkins et al. | |
| D598,556 S | 8/2009 | Chen | |
| D608,006 S | 1/2010 | Avitable et al. | |
| D613,870 S | 4/2010 | Shust | |
| D635,682 S | 4/2011 | Chiang | |
| 7,927,259 B1 | 4/2011 | Rix | |
| 7,927,294 B2 | 4/2011 | Kamimura et al. | |
| D638,948 S | 5/2011 | Janzon | |
| D659,644 S | 5/2012 | Gretz | |
| 8,313,450 B2 | 11/2012 | Ben-Nun | |
| D678,531 S | 3/2013 | Patil | |
| D695,902 S | 12/2013 | Daniels et al. | |
| 8,622,943 B2 | 1/2014 | Ben-Nun | |
| D704,848 S | 5/2014 | Thomas et al. | |
| 8,764,688 B1 | 7/2014 | Nauman et al. | |
| 8,777,881 B2 | 7/2014 | Tsai | |
| D712,052 S | 8/2014 | Thomas et al. | |
| D716,457 S | 10/2014 | Brefka et al. | |
| 9,017,273 B2 | 4/2015 | Burbank et al. | |
| D735,873 S | 8/2015 | Brefka et al. | |
| 9,125,442 B2 | 9/2015 | Brown | |
| D751,720 S | 3/2016 | Williams | |
| D754,355 S | 4/2016 | Ganapathy et al. | |
| D756,180 S | 5/2016 | Chen | |
| D762,869 S | 8/2016 | Beckman et al. | |
| D764,672 S | 8/2016 | Vosch et al. | |
| 9,414,954 B2 | 8/2016 | Brown | |
| 9,549,870 B2 | 1/2017 | Shafieloo | |
| D786,447 S | 5/2017 | Bigelow et al. | |
| D800,326 S | 10/2017 | Cox | |
| 9,849,024 B2 | 12/2017 | Mandel | |
| D806,888 S | 1/2018 | Cheng et al. | |
| D810,311 S | 2/2018 | Chen | |
| D811,613 S | 2/2018 | Marton et al. | |
| D811,614 S | 2/2018 | Marton et al. | |
| 9,889,066 B2 | 2/2018 | Danby et al. | |
| 9,901,510 B2 | 2/2018 | Smith | |
| D817,732 S | 5/2018 | Rettler | |
| D820,994 S | 6/2018 | Trapp | |
| D822,221 S | 7/2018 | Huth et al. | |
| D831,221 S | 10/2018 | Smith | |
| 10,123,937 B2 | 11/2018 | Pisharodi et al. | |
| 10,159,623 B2 | 12/2018 | Leftly | |
| D837,394 S | 1/2019 | Cryan et al. | |
| D837,395 S | 1/2019 | Gan | |
| D841,178 S | 2/2019 | Lazarides et al. | |
| D841,825 S | 2/2019 | Rogers | |
| 10,245,208 B2 | 4/2019 | Macguinness | |
| 10,314,762 B1 | 6/2019 | Marton et al. | |
| 10,406,024 B2 | 9/2019 | Evans et al. | |
| D863,573 S | 10/2019 | Ito et al. | |
| D865,986 S | 11/2019 | Cryan et al. | |
| 10,493,264 B1 | 12/2019 | Lefkovitz | |
| 10,555,681 B2 | 2/2020 | Sun | |
| 10,632,040 B2 | 4/2020 | Muench et al. | |
| D886,302 S | 6/2020 | Raghavan et al. | |
| D890,933 S | 7/2020 | Shurtliff et al. | |
| D891,626 S | 7/2020 | Xu | |
| 10,779,764 B2 | 9/2020 | Marlinski | |
| D905,253 S | 12/2020 | Hubelbank | |
| D910,858 S | 2/2021 | Marton et al. | |
| D917,054 S | 4/2021 | Woo | |
| D923,184 S | 6/2021 | Li | |
| D928,974 S | 8/2021 | Zulkosky et al. | |
| D932,035 S | 9/2021 | McDonough et al. | |
| D932,042 S | 9/2021 | Hu | |
| D932,638 S | 10/2021 | McDonough et al. | |
| D932,639 S | 10/2021 | McDonough et al. | |
| D932,640 S | 10/2021 | McDonough et al. | |
| D937,426 S | 11/2021 | Cordle | |
| D950,740 S | 5/2022 | Caneppele et al. | |
| D953,550 S | 5/2022 | Li | |
| D957,651 S | 7/2022 | Williams et al. | |
| D957,654 S | 7/2022 | Savchuk | |
| D961,889 S | 8/2022 | Chen | |
| 11,771,587 B1 * | 10/2023 | Maunder | H05B 3/34 607/96 |
| 11,815,098 B1 * | 11/2023 | Patil | F25B 21/02 |
| 11,940,163 B1 | 3/2024 | Nazarian et al. | |
| 2001/0007952 A1 * | 7/2001 | Shimizu | A61F 7/02 607/109 |
| 2005/0075593 A1 | 4/2005 | Smith et al. | |
| 2005/0193742 A1 | 9/2005 | Arnold | |
| 2007/0255187 A1 | 11/2007 | Branch | |
| 2008/0188915 A1 | 8/2008 | Mills et al. | |
| 2010/0249637 A1 | 9/2010 | Walter et al. | |
| 2010/0274162 A1 * | 10/2010 | Evans | A61H 15/0092 601/46 |
| 2011/0000516 A1 | 1/2011 | Hershberger et al. | |
| 2011/0233185 A1 | 9/2011 | Augustine et al. | |
| 2012/0023785 A1 | 2/2012 | Barnes et al. | |
| 2013/0085552 A1 | 4/2013 | Mandel | |
| 2013/0238043 A1 * | 9/2013 | Beardall | A61F 7/007 607/3 |
| 2014/0316311 A1 | 10/2014 | Nauman et al. | |
| 2014/0350441 A1 | 11/2014 | Shafieloo | |
| 2014/0364778 A1 | 12/2014 | Leftly et al. | |
| 2015/0121900 A1 * | 5/2015 | Yamazaki | A45D 44/00 62/3.3 |
| 2015/0174002 A1 | 6/2015 | Burbank et al. | |
| 2015/0223975 A1 | 8/2015 | Anderson et al. | |
| 2016/0058657 A1 | 3/2016 | Lal et al. | |
| 2016/0089299 A1 | 3/2016 | Munoz | |
| 2016/0228325 A1 | 8/2016 | Kologrivov et al. | |
| 2016/0242956 A1 * | 8/2016 | Pilby Gomez | A61F 7/12 |
| 2016/0331631 A1 | 11/2016 | Odi | |
| 2016/0346153 A1 | 12/2016 | Hodges, IV | |
| 2016/0367425 A1 | 12/2016 | Wersland | |
| 2017/0042754 A1 | 2/2017 | Fowers et al. | |
| 2017/0113039 A1 | 4/2017 | Tuan | |
| 2017/0119620 A1 | 5/2017 | Trapp | |
| 2017/0290736 A1 | 10/2017 | Idris | |
| 2017/0304145 A1 | 10/2017 | Pepe | |
| 2018/0042810 A1 | 2/2018 | Nguyen | |
| 2018/0065517 A1 | 3/2018 | Kuhley et al. | |
| 2018/0140506 A1 | 5/2018 | Smith et al. | |

(56) References Cited

U.S. PATENT DOCUMENTS

| | | | |
|---|---|---|---|
| 2018/0141188 | A1 | 5/2018 | Lai |
| 2018/0147086 | A1 | 5/2018 | Evans et al. |
| 2018/0228689 | A1 | 8/2018 | Lach et al. |
| 2018/0303704 | A1 | 10/2018 | Idris |
| 2019/0070068 | A1 | 3/2019 | Pisharodi et al. |
| 2019/0099290 | A1 | 4/2019 | Thomas et al. |
| 2019/0151190 | A1 | 5/2019 | Burbank et al. |
| 2019/0162460 | A1* | 5/2019 | Oh .................. F25B 21/02 |
| 2019/0183724 | A1 | 6/2019 | Sifferlin |
| 2019/0290531 | A1* | 9/2019 | Bosma .................. A61H 7/00 |
| 2019/0350752 | A1* | 11/2019 | Aguiar .................. A61F 7/02 |
| 2020/0061316 | A1 | 2/2020 | Inoue et al. |
| 2020/0068964 | A1 | 3/2020 | Brandt et al. |
| 2020/0078261 | A1 | 3/2020 | Duvall |
| 2020/0113773 | A1 | 4/2020 | Ramanan et al. |
| 2020/0214927 | A1 | 7/2020 | Clowney et al. |
| 2020/0224964 | A1* | 7/2020 | Alexander .......... F25D 11/003 |
| 2020/0230021 | A1 | 7/2020 | Pisharodi et al. |
| 2020/0253813 | A1 | 8/2020 | Kuhns |
| 2020/0368061 | A1 | 11/2020 | Levinson et al. |
| 2021/0236328 | A1* | 8/2021 | Popielarski .......... A61F 7/0085 |
| 2021/0298812 | A1* | 9/2021 | Sverdlik .............. A61B 18/08 |
| 2021/0330539 | A1 | 10/2021 | Faussett |
| 2021/0338478 | A1* | 11/2021 | Kim .................. A61F 7/00 |
| 2022/0110821 | A1* | 4/2022 | Aguiar ................ A61H 9/0078 |
| 2022/0125672 | A1* | 4/2022 | Wersland ........... A61H 23/0254 |
| 2022/0168170 | A1* | 6/2022 | Bell .................. A61F 7/007 |
| 2022/0192868 | A1* | 6/2022 | Wersland .............. A61F 7/02 |
| 2022/0249277 | A1* | 8/2022 | Hwang .............. A61F 7/007 |
| 2022/0265467 | A1* | 8/2022 | Monazami .......... A61F 7/0085 |
| 2022/0287873 | A1* | 9/2022 | Taslagyan ........... A61F 7/007 |
| 2022/0331135 | A1* | 10/2022 | Gengrinovitch ...... A61F 7/007 |
| 2022/0362097 | A1* | 11/2022 | Hart .................. A61F 7/007 |
| 2022/0378604 | A1* | 12/2022 | Lee .................. H02J 50/10 |
| 2023/0017326 | A1* | 1/2023 | Alexander ............ F25B 21/02 |
| 2023/0074407 | A1* | 3/2023 | Wersland .............. A61H 23/02 |
| 2023/0084903 | A1* | 3/2023 | Marton ................ A61H 23/02 |
| | | | 601/18 |
| 2023/0157867 | A1* | 5/2023 | Aguiar .................. A61F 7/02 |
| | | | 607/108 |
| 2023/0173278 | A1* | 6/2023 | Wang ................ A61N 1/36034 |
| 2023/0329902 | A1* | 10/2023 | Aguiar ................ A61H 9/0092 |
| 2023/0372730 | A1* | 11/2023 | Yu .................... A61N 1/0408 |
| 2023/0400233 | A1* | 12/2023 | Jakobsen ............ F25D 31/007 |
| 2024/0125523 | A1* | 4/2024 | Zhou .................. A61N 5/0616 |
| 2024/0230170 | A1* | 7/2024 | Che .................... F25B 21/02 |
| 2024/0350834 | A1* | 10/2024 | Kang ................ A61N 1/36021 |
| 2024/0398612 | A1* | 12/2024 | Dickinson ............ A61F 7/007 |
| 2024/0431076 | A1* | 12/2024 | Seo .................. H05K 7/20272 |
| 2025/0017765 | A1* | 1/2025 | Ross .................. A63B 22/0664 |

FOREIGN PATENT DOCUMENTS

| | | | | |
|---|---|---|---|---|
| CN | 301664182 | S | 9/2011 | |
| CN | 301695895 | | 10/2011 | |
| CN | 301771075 | | 12/2011 | |
| CN | 202637439 | U | 1/2013 | |
| CN | 103284874 | A | 9/2013 | |
| CN | 303250924 | S | 6/2015 | |
| CN | 303250929 | S | 6/2015 | |
| CN | 104984624 | A * | 10/2015 | |
| CN | 303679907 | | 5/2016 | |
| CN | 205561041 | U * | 9/2016 | ............ F24F 1/02 |
| CN | 304091502 | | 3/2017 | |
| CN | 106691810 | A | 5/2017 | |
| CN | 304124110 | | 5/2017 | |
| CN | 106859949 | A | 6/2017 | |
| CN | 304223351 | | 7/2017 | |
| CN | 304334066 | | 10/2017 | |
| CN | 304364250 | | 11/2017 | |
| CN | 304561844 | S | 3/2018 | |
| CN | 108514470 | A | 9/2018 | |
| CN | 207855923 | U | 9/2018 | |
| CN | 109528473 | A | 3/2019 | |
| CN | 305105930 | | 4/2019 | |
| CN | 305121011 | | 4/2019 | |
| CN | 305493698 | | 12/2019 | |
| CN | 305493699 | | 12/2019 | |
| CN | 305511388 | | 12/2019 | |
| CN | 305531856 | | 1/2020 | |
| CN | 305539686 | | 1/2020 | |
| CN | 305635976 | | 3/2020 | |
| CN | 305795905 | | 5/2020 | |
| CN | 305796012 | | 5/2020 | |
| CN | 305796013 | | 5/2020 | |
| CN | 306006372 | | 8/2020 | |
| CN | 306067989 | | 9/2020 | |
| CN | 306068005 | | 9/2020 | |
| CN | 306073089 | | 9/2020 | |
| CN | 306606113 | | 6/2021 | |
| CN | 306651421 | | 6/2021 | |
| CN | 306981442 | | 12/2021 | |
| CN | 306981451 | | 12/2021 | |
| CN | 307029685 | | 12/2021 | |
| CN | 114216172 | A * | 3/2022 | |
| CN | 307633505 | | 11/2022 | |
| CN | 307653347 | | 11/2022 | |
| EM | EU008789861-0001 | | 12/2021 | |
| EM | EU009010564-0001 | | 5/2022 | |
| EM | EU009010564-0002 | | 5/2022 | |
| EM | EU009010564-0006 | | 5/2022 | |
| EM | EU009010564-0007 | | 5/2022 | |
| HK | 2117964 | | 12/2021 | |
| JP | S5428491 | A | 3/1979 | |
| JP | H0447440 | U | 4/1992 | |
| JP | 2000189525 | A | 7/2000 | |
| JP | D1086129 | | 9/2000 | |
| JP | D1355211 | | 4/2009 | |
| JP | D1355212 | | 4/2009 | |
| JP | D1395716 | | 8/2010 | |
| JP | 2011502369 | A | 1/2011 | |
| JP | D1444377 | | 6/2012 | |
| JP | D1456095 | | 11/2012 | |
| JP | 5129032 | B2 | 1/2013 | |
| JP | D1483906 | | 11/2013 | |
| JP | 2014511240 | A | 5/2014 | |
| JP | D1562309 | | 11/2016 | |
| JP | D1625637 | | 3/2019 | |
| JP | D1635963 | | 7/2019 | |
| JP | 3230942 | U | 3/2021 | |
| KR | 200197414 | Y1 | 11/2000 | |
| KR | 300388708.0001 | | 8/2006 | |
| KR | 20090005341 | U | 6/2009 | |
| KR | 100992766 | B1 | 11/2010 | |
| KR | 101162978 | B1 | 7/2012 | |
| KR | 300659290 | | 9/2012 | |
| KR | 300685526 | | 3/2013 | |
| KR | 300688355 | | 4/2013 | |
| KR | 300777431 | | 12/2014 | |
| KR | 300786426 | | 3/2015 | |
| KR | 20170108550 | A | 9/2017 | |
| KR | 300941258 | | 1/2018 | |
| KR | 300959951 | | 6/2018 | |
| KR | 301075396 | | 9/2020 | |
| KR | 301082314 | | 11/2020 | |
| KR | 301109767 | | 5/2021 | |
| KR | 301165063 | | 5/2022 | |
| RU | 00129403 | | 1/2022 | |
| TW | I359657 | B | 3/2012 | |
| WO | WO-2015145471 | A1 | 10/2015 | |
| WO | WO-2017045909 | A1 * | 3/2017 | ............ F24F 1/022 |
| WO | WO-2018064220 | A1 | 4/2018 | |
| WO | WO-2023034824 | A1 | 3/2023 | |

OTHER PUBLICATIONS

Amazon: "RecoveryTherm Back—Hot Vibration Back and Core Wrap for Athletes—Advanced Hot Vibration for Back Pain Relief Wrap with Cryothermal Technology—One Size Fits All", Date First Available on Sep. 20, 2022, 02 Pages, Retrieved from URL: https://www.amazon.com/RecoveryTherm-Back-Vibration-

(56) References Cited

OTHER PUBLICATIONS

Cryothermal-Technology/dp/BOB8GRL7LR/ref=cm_cr_arp_d_product_top?ie=UTF8.

Amazon: "RecoveryTherm Knee—Contrast Therapy Wrap—Hot & Cold Vibration Recovery Knee Wrap for Athletes—Advanced Contrast Therapy for Knee Pain Relief Wrap with Cryothermal Technology—One Size Fits All," Date First Available on Aug. 3, 2022, 03 Pages, Retrieved from URL: https://www.amazon.com/RecoveryTherm-Knee-Vibration-Cryothermal-Technology/dp/BOB8GCB/YF/ref=cm_cr_arp_d_product_topie=UTF8.

Anthony Katz, "The RAPTOR: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Defendant's Initial Invalidity Contentions, *Therabody, Inc.* v. *Tzumi Electronics LLC* et al., Case No. SDNY-1-21-cv-07803 (PGG)(RWL), dated Aug. 17, 2022; 16 pages.

Description of Therabody GI Device, available at: https://www.therabody.com/US/en-us/faq/thearagun-devices/faq-devices-1.html?fdid=faq&csortb1=sortOrder&csortd1=1 (last visited Feb. 15, 2023).

fsastore.com: "Battle Creek Embrace Relief Knee Wrap," Available at least as early as 2020, 2021, 19 Pages, Retrieved from URL: https://fsastore.com/battle-creek-embrace-relief-knee-wrap/29568.html.

Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.

Hotsnapz: "Back Belt Set with Free Extra Reusable Heat Pad," hotsnapz.com, Available at least as early as 2022, 11 Pages, Retrieved from URL: https://hotsnapz.com/products/hotsnapz-back-belt-set-with-free-extra-heat-pack.

hyperice.com: "Hyperice X," Available at least as early as Sep. 8, 2021, 10 Pages, Retrieved from URL: https://hyperice.com/products/hyperice-x//?wickedsource=google&wickedid=EAlalQ.obChMIo_D5z_-4-wIV9Y5bCh284gf8EAQ.YByABEgLiRvD_BwE&wickedid=&wcid=17299137048&wv=4&gclid=EAlalQobChMIo_D5z_-4-wIV9Y5bCh284gf8EAQ.YByABEgLiRvD_BwE.

International Search Report and Written Opinion for International Application No. PCT/US2021/064027, mailed Mar. 10, 2022, 19 Pages.

International Search Report and Written Opinion for International Application No. PCT/US2021/064048, mailed Mar. 9, 2022, 9 Pages.

International Search Report and Written Opinion for International Application No. PCT/US2022/075699, mailed Jan. 11, 2023, 8 Pages.

KT Tape: "KT Recovery+ Ice/Heat Wrap," kttape.com, Available at least as early as Jun. 21, 2021, 06 Pages, Retrieved from URL: https://www.kttape.com/products/kt-recovery-ice-heat-wrap.

Therabody: "RecoveryTherm Hot and Cold Vibration Knee," Accessed on Jan. 30, 2023, 03 Pages, Retrieved from URL: https://www.therabody.com/us/en-us/recoverytherm-knee-massager-compression.htmlcgid=therabody-recovery-devices#start=1.

Therabody: "RecoveryTherm Hot Vibration Back and Core Wrap for Athletes—Advanced Hot Vibration for Back Pain Relief Wrap with Cryothermal Technology—One Size Fits All," Accessed on Jan. 30, 2023, 02 Pages, Retrieved from URL: https://www.therabody.com/us/en-us/recoverytherm-core-lower-back-massager-compression.html?cgid=therabody-recovery-devices#start=1.

Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.

Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.

Youtube: "Therabody RecoveryTherm Knee Sleeve Review—Hot, Cold, Vibration," Published on Dec. 22, 2022, 01 Page, Retrieved from URL: https://www.youtube.com/watch?v=-dHbFc_LJfw.

International Search Report and Written Opinion of the International Searching Authority, directed to related International Patent Application No. PCT/US2024/035629, mailed Nov. 13, 2024, 20 pages.

* cited by examiner

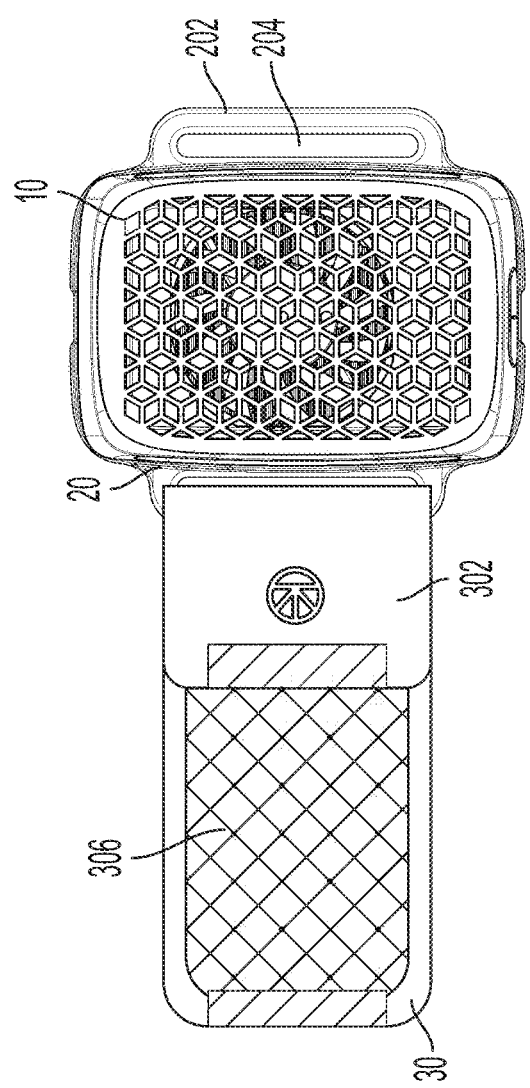
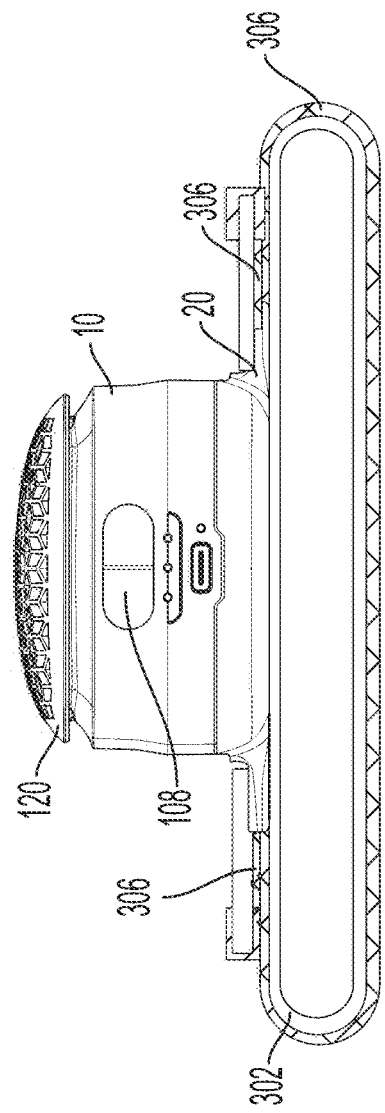
FIG. 21A
FIG. 21B

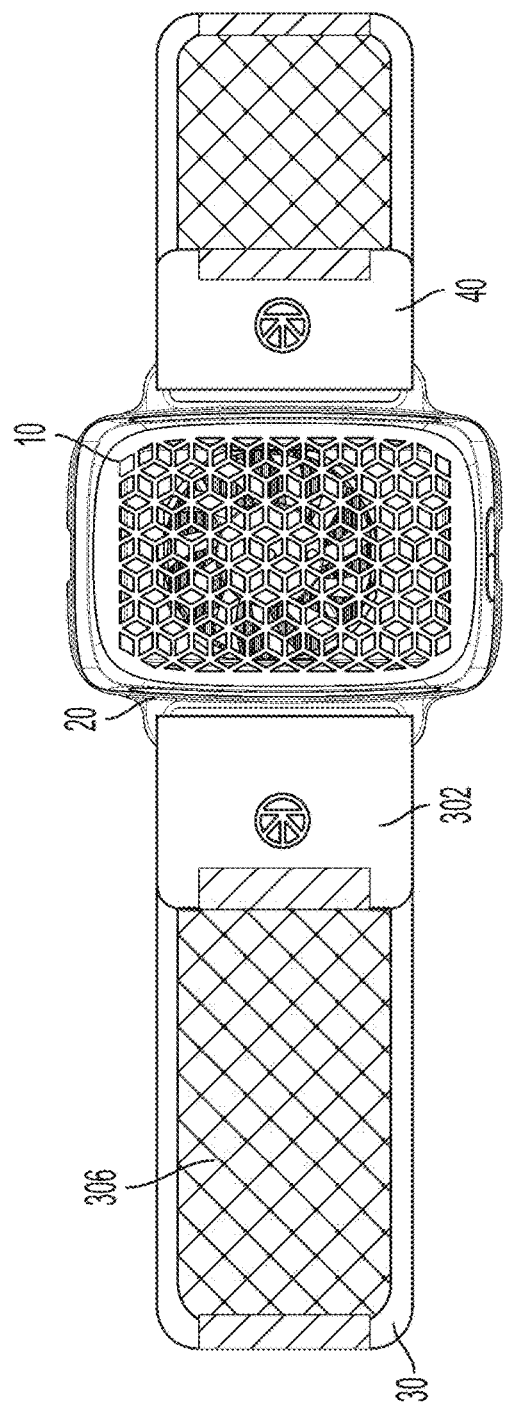
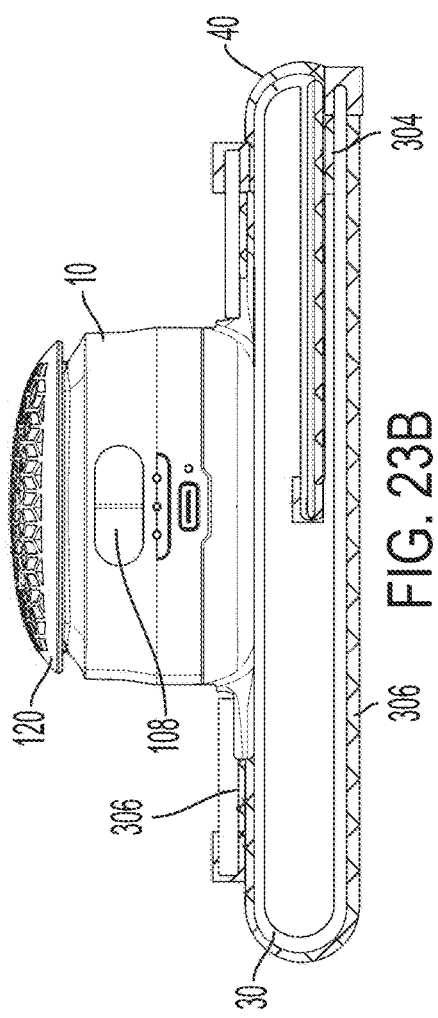
FIG. 23A
FIG. 23B

PORTABLE TEMPERATURE CONTROLLED DEVICE

CROSS-REFERENCE TO RELATED APPLICATIONS

This application is a continuation of U.S. application Ser. No. 18/362,349, filed Jul. 31, 2023, the entirety of which is incorporated herein by reference.

TECHNICAL FIELD

The present disclosure relates to a temperature-controlled device, more specifically, a hand-held portable temperature-controlled device.

BACKGROUND

Cooling and heating devices are used for therapeutic purposes or during surgical procedures due to many known benefits of hot and/or cold therapy in treatment. Accordingly, various apparatuses have been devised to achieve the desired heat and/or cold transfer. One issue with current heating and/or cooling devices is lack of portability and maneuverability. Bulky devices are often used to heat and cool the affected areas to provide fast and efficient heat transfer. The size of these devices is typically necessary because components are not optimally arranged or configured to promote efficient operation. These heating and cooling devices are often heavy, need to be in a fixed position, and plugged into a continuous power supply. Smaller and lighter multi-therapy devices are desirable. One potential hurdle to a smaller form factor has been managing heat dissipation within a portable device to protect the internal components from overheating. Accordingly, a need exists for a light portable device that provides heating and cooling therapy comparable to the bulky device while also providing efficient heat management. It is further desirable to provide a versatile multi-therapy device that can be used on different body parts of a user, whether manually by the user or, if desired, in a fixed position.

The background description disclosed anywhere in this patent application includes information that may be useful in understanding the present disclosure. It is not an admission that any of the information provided herein is prior art or relevant to the presently claimed concepts, or that any publication specifically or implicitly referenced is prior art.

SUMMARY

Described herein is a novel portable temperature-controlled device for therapeutic applications including both cold and heat therapies within a compact and handheld device. In some aspects, the portable temperature-controlled device is assembled with an adjustable strap system to wrap around a patient body part. The temperature-controlled device is designed to have an ergonomic configuration to be comfortably held by one hand, while placing the device on a desired area of the body. These areas can include the back, knee, elbow, shoulder, ankle, etc. The temperature-controlled device can be further assembled with a strap to secure on the body part to free the user's hand.

The temperature-controlled device can include a thermoelectric element to transfer heating and cooling to the user's body. In a typical implementation, the thermoelectric element is a device that utilizes the Peltier Effect, having one side of which cools while the other side heats. The heating and cooling modes can be optionally and selectively switched within predetermined temperature ranges. The temperature-controlled device can further include a rechargeable battery for prolonged use.

In one aspect, a hand-held portable temperature-controlled device includes a housing having a generally cuboid shape with curved surfaces and configured to be grasped by one hand. The housing may include: a controllable temperature element having a first surface and a second surface and configured to generate cooling and heating; a heat sink disposed on the first surface of the controllable temperature element; a fan disposed on the heat sink and configured to direct heat away from the heat sink; a heat spreader comprising a first side and a second side, the first side extending out from the housing and contacting a user's body part; a support member configured to support the heat sink and the fan; and a temperature controller connected to the controllable temperature element. The housing further includes a first air inlet configured to permit air flow into the housing and an air outlet configured to permit air flow to flow out of the housing, and the first air inlet and the air outlet are in fluid communication with each other.

In another aspect, a wearable assembly includes a temperature-controlled device which comprises a housing having a generally cuboid shape. The housing may include: a controllable temperature element having a first surface and a second surface; a heat sink disposed on the first surface of the controllable temperature element; a fan disposed on the heat sink and configured to direct heat away from the heat sink; a heat spreader comprising one side and another side and configured to receive thermal energy from the controllable temperature element; and a support member configured to support at least one battery, the heat sink, and the fan. The wearable assembly includes a strap case configured to be assembled to the temperature-controlled device. The strap case may comprise: a center opening through which the heat spreader extends on a bottom side; and a pair of side arms curvedly, integrally extending upward, each having a protrusion protruding toward the center opening.

Further features and advantages, as well as the structure and operation of various aspects, are described in detail below with reference to the accompanying drawings. It is noted that the specific aspects described herein are not intended to be limiting. Such aspects are presented herein for illustrative purposes only. Additional aspects will be apparent to persons skilled in the relevant art(s) based on the teachings contained herein.

BRIEF DESCRIPTION OF THE DRAWINGS

The accompanying drawings, which are incorporated herein and form a part of the specification, illustrate aspects of the present disclosure and, together with the description, further serve to explain the principles of the disclosure and to enable a person skilled in the pertinent art to make and use the disclosure.

FIGS. 21A and 21B are top and side views of the portable therapeutic temperature-controlled device assembled with the primary strap.

FIGS. 23A and 23B are top and side views of the portable therapeutic temperature-controlled device assembled with the primary strap and the secondary strap.

In the drawings, like reference numbers generally indicate identical or similar elements. Additionally, generally, the left-most digit(s) of a reference number identifies the drawing in which the reference number first appears.

DETAILED DESCRIPTION

Figure 1:
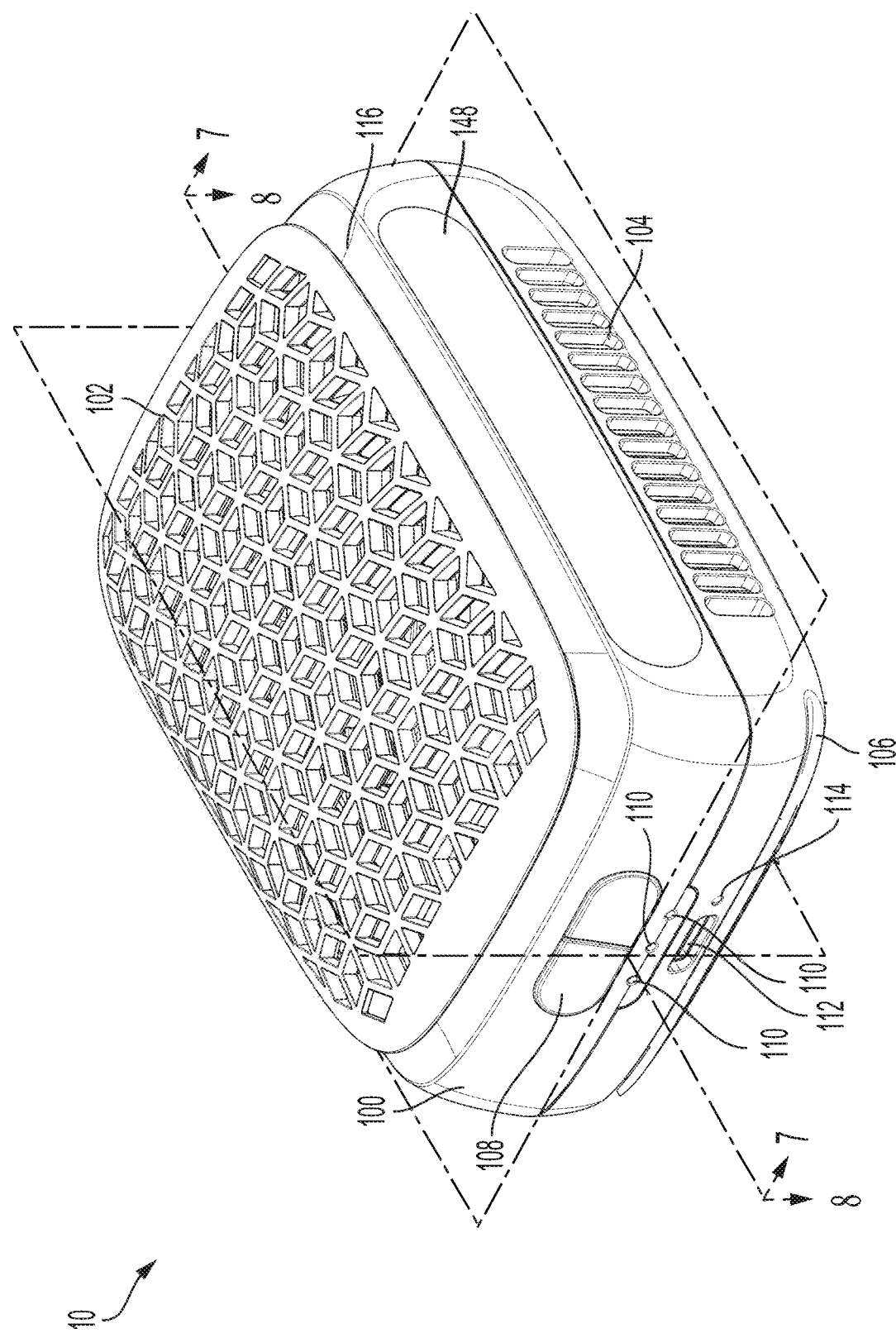
FIG. 1 is a perspective view of a portable therapeutic temperature-controlled device according to aspects of the present disclosure.

The following description and drawings are illustrative and are not to be construed as limiting. Numerous specific details are described to provide a thorough understanding of the disclosure. However, in certain instances, well-known or conventional details are not described in order to avoid obscuring the description. References to one or more aspects in the present disclosure can be, but not necessarily are references to the same aspect; and, such references mean at least one of the aspects. If a component is not shown in a drawing then this provides support for a negative limitation in the claims stating that that component is "not" present. However, the above statement is not limiting and in another aspect, the missing component can be included in a claimed aspect.

Reference in this specification to "one aspect," "an aspect," "a preferred aspect" or any other phrase mentioning the word "aspect" means that a particular feature, structure, or characteristic described in connection with the aspect is included in at least one aspect of the-disclosure and also means that any particular feature, structure, or characteristic described in connection with one aspect can be included in any aspect or can be omitted or excluded from any aspect. The appearances of the phrase "in one aspect" in various places in the specification are not necessarily all referring to the same aspect, nor are separate or alternative aspects mutually exclusive of other aspects. Moreover, various features are described which may be exhibited by some aspects and not by others and may be omitted from any aspect. Furthermore, any particular feature, structure, or characteristic described herein may be optional. Similarly, various requirements are described which may be requirements for some aspects but not other aspects. Where appropriate any of the features discussed herein in relation to one aspect or aspect of the disclosure may be applied to another aspect or aspect of the disclosure. Similarly, where appropriate any of the features discussed herein in relation to one aspect or aspect of the disclosure may be optional with respect to and/or omitted from that aspect or aspect of the disclosure or any other aspect or aspect of the disclosure discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various aspects given in this specification.

Without intent to further limit the scope of the disclosure, examples of instruments, apparatus, methods and their related results according to the aspects of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down,"

"aft," "forward," "inboard," "outboard" and "below" used herein are merely for case of description and refer to the orientation of the components as shown in the figures. It should be understood that any orientation of the components described herein is within the scope of the present disclosure.

The terms "connected" or "coupled" and related terms are used in an operational sense and are not necessarily limited to a direct connection or coupling. The term "thermally coupled" means coupled in a way capable of conducting heat, and the term "thermally insulated" means separated by a substance that deters heat transfer.

The term "flexible" generally means bendable and adaptable under relatively little force. In the context of various aspects of the present disclosure, flexible is intended to describe the dynamic conforming nature of the personal temperature controlled device to the general shape of a portion of a person's body, such as wrist, ankle, neck, shoulder, back, chest, forehead, rib cage, arch, temple, palm, etc., directly or indirectly in contact with or otherwise engaging a surface of the personal temperature-controlled device. In addition, the term "approximately" is generally used to modify a numerical value above and below the set value by a variation of +/−10%.

Figure 9:
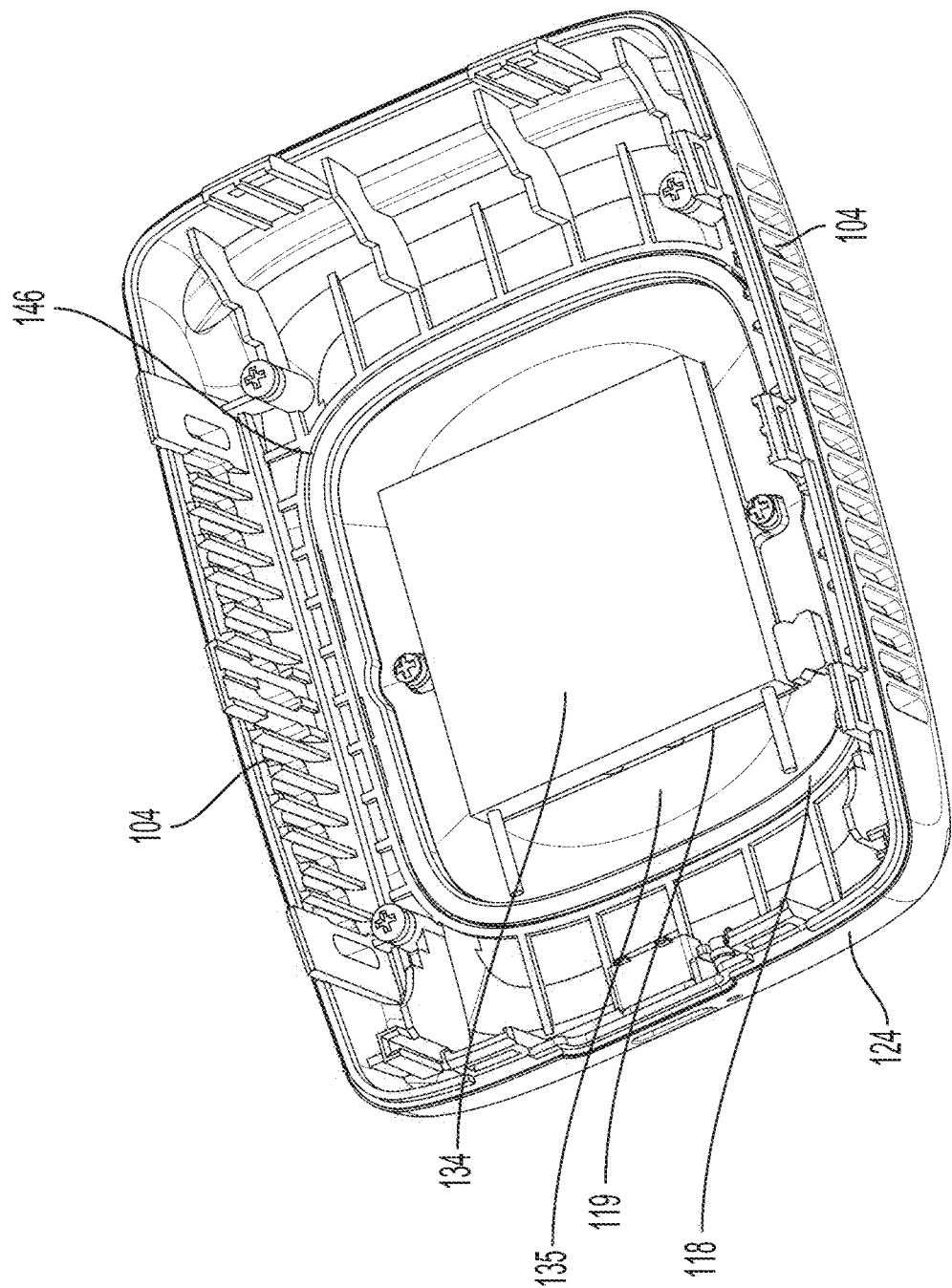
FIG. 9 is an interior of a lower housing of the portable therapeutic temperature-controlled device according to aspects of the present disclosure.
Figure 10:
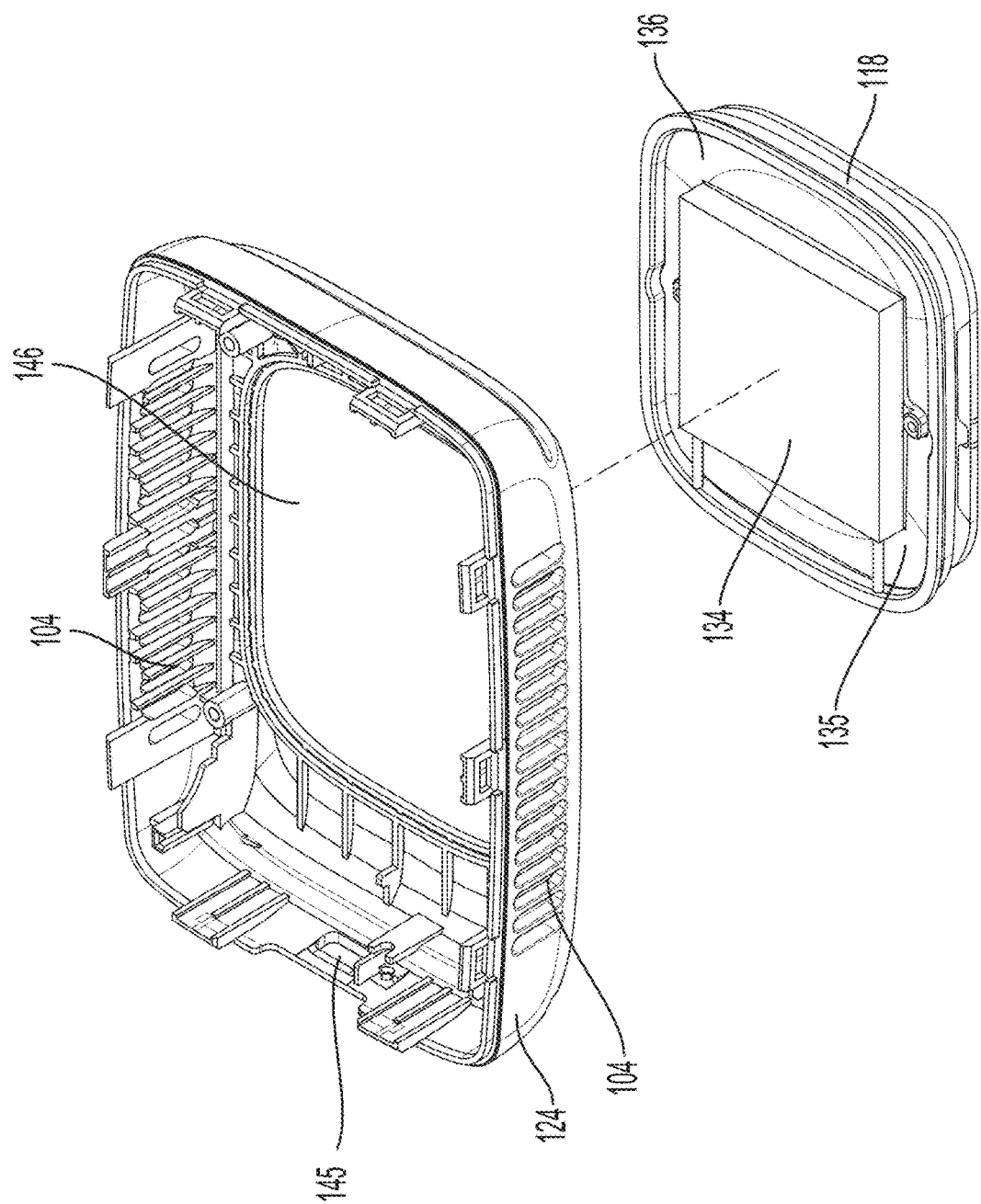
FIG. 10 is an exploded view of FIG. 9.
Figure 11:
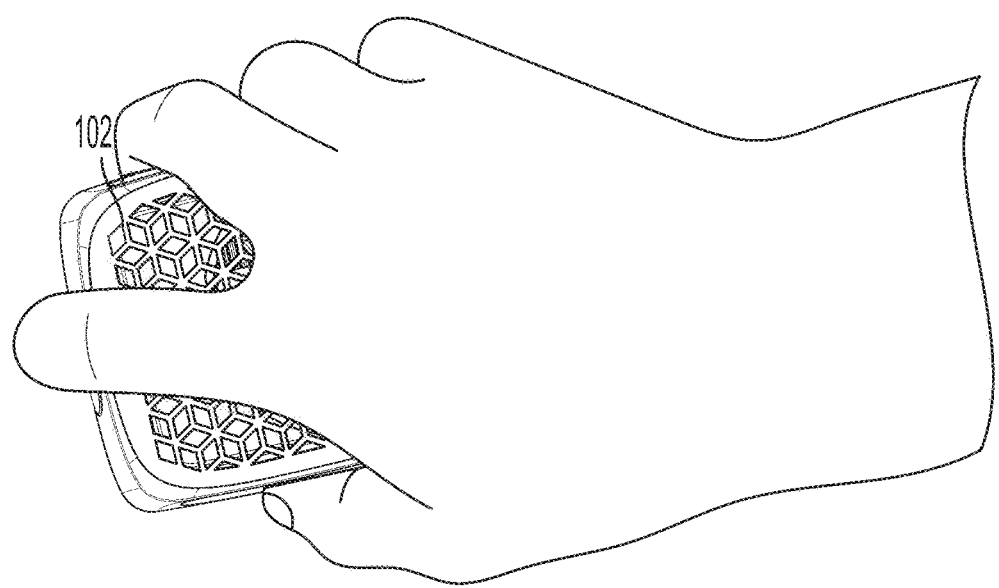
FIG. 11 is a top view of the portable therapeutic temperature-controlled device grasped by a user's hand.
Figure 12:
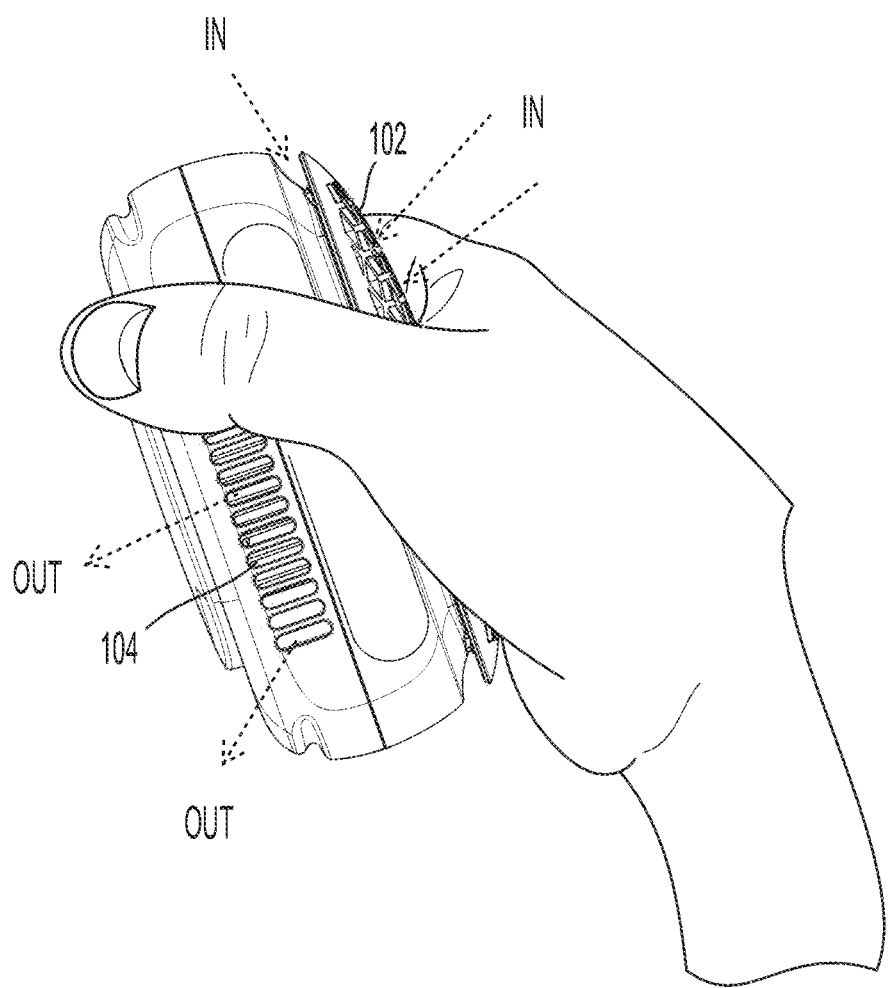
FIG. 12 is a side view of the portable therapeutic temperature-controlled device grasped by a user's hand.

Described herein and shown in FIGS. 1-10 is an exemplary temperature-controlled device that can provide cooling and heating effects. FIGS. 11 and 12 show the temperature-controlled device grasped by a user's hand.

FIG. 1 shows a temperature-controlled device 10 designed for a user to comfortably grasp by one hand while providing a heating or cooling therapeutic effect to a desired area on the user's body and also promoting air flow into and out of the temperature-controlled device 10. In some aspects, the temperature-controlled device 10 includes a housing 100, on an outer side of which includes an air inlet or a first air inlet 102 on a top surface of the temperature-controlled device 10, an air outlet 104 on at least one side surface (e.g., at least one of a first side surface or a second side surface of the temperature-controlled device 10, a pair of recesses 106 on opposing side surfaces, a plurality of buttons 108 for selectively controlling a heating mode and a cooling mode of a temperature mode by user manipulation, a first or control mode Light-Emitting Diode (LED) 110 disposed below the buttons 108 for indicating the temperature mode, a Universal Serial Bus (USB) charging port or simply charging port 112, a second or battery level LED 114, and an undercut 116. In some aspects, the first LED 110 may include one or more LEDs. In some aspects, the overall shape of the housing 100 may be curvedly shaped and dimensioned for ergonomic holding by a user's hand. In further aspects, each element of the temperature-controlled device 10 is arranged and designed to provide efficient operation of the heating and cooling effect and optimal heat dissipation in a compact space, as will be described later. For example, the housing 100 may be rectangular in shape to allow for one-handed holding while maximizing the size of air inlet 102.

Figure 2:
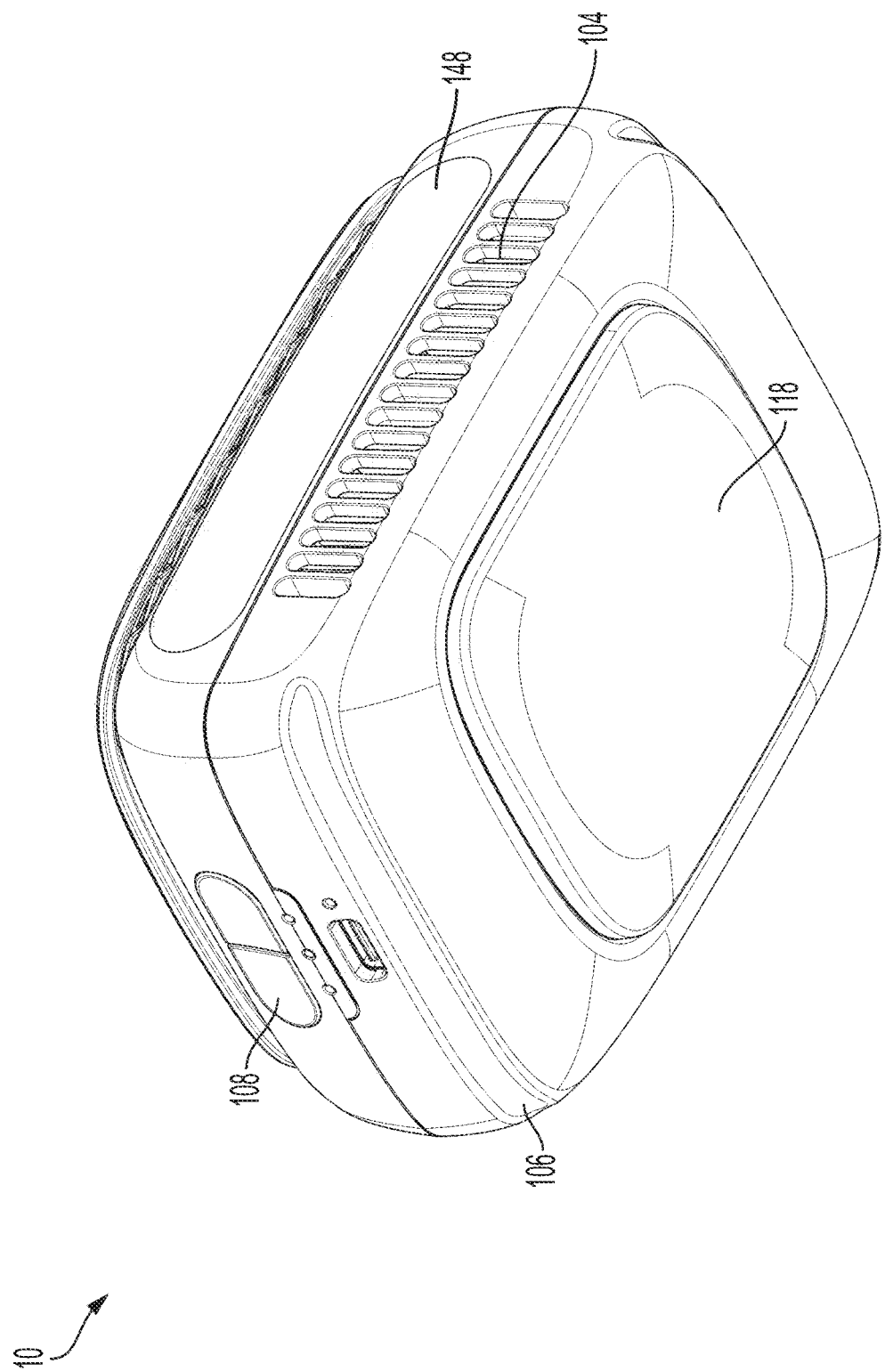
FIG. 2 is another perspective view of the portable therapeutic temperature-controlled device according to aspects of the present disclosure.
Figure 3:
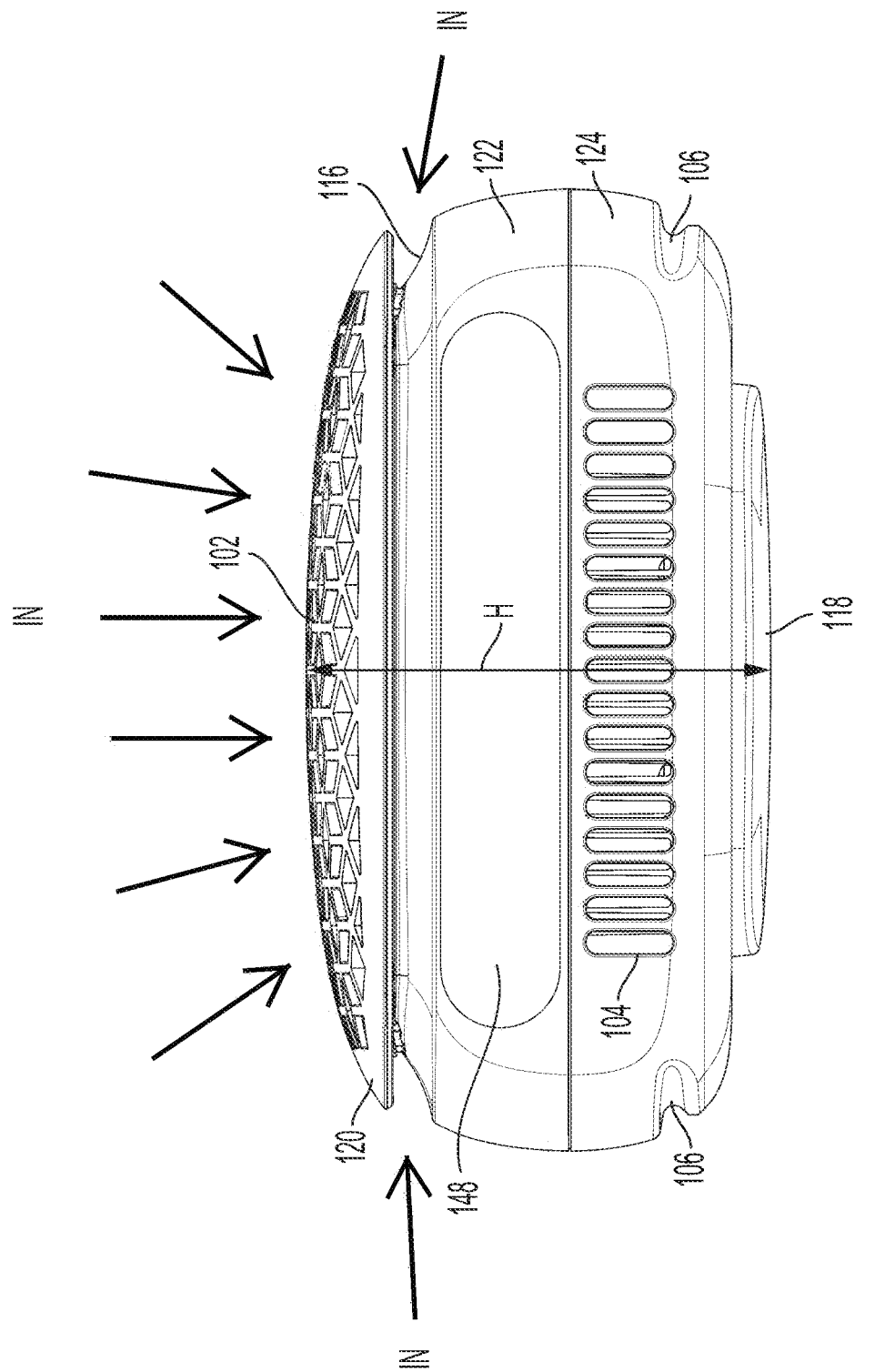
FIG. 3 is a side view of the portable therapeutic temperature-controlled device according to aspects of the present disclosure.

Referring to FIGS. 2 and 3, in some aspects, the temperature-controlled device 10 further includes a heat spreader 118 on the bottom side of the housing 100. In some aspects, the heat spreader 118 may be implemented as a metallic heat spreader and can be made of high thermal conductive materials, such as, for example, copper, aluminum, or other metals or metal alloys, or certain ceramics, to help transfer heat or cold to increase the effective area of heating or cooling treatment. As will be described later, the housing 100 has an opening (e.g., "146" in FIGS. 6 and 10) defined in the bottom side of the housing 100 through which the heat spreader 118 extends out of the housing 100. While the housing 100 may be formed of, e.g., a plastic material, the bottom portion of the housing 100 exposes the heat spreader 118, which in some aspects may be constructed of a metal material. Thus, the heat spreader 118 may have one side exposed outside that can directly transfer thermal energy to a body part of the user. In addition, this configuration allows engagement with a strap case, which will be described later, while ensuring that the exposed side of the heat spreader 118 maintains direct contact with the user's skin.

Figure 4:
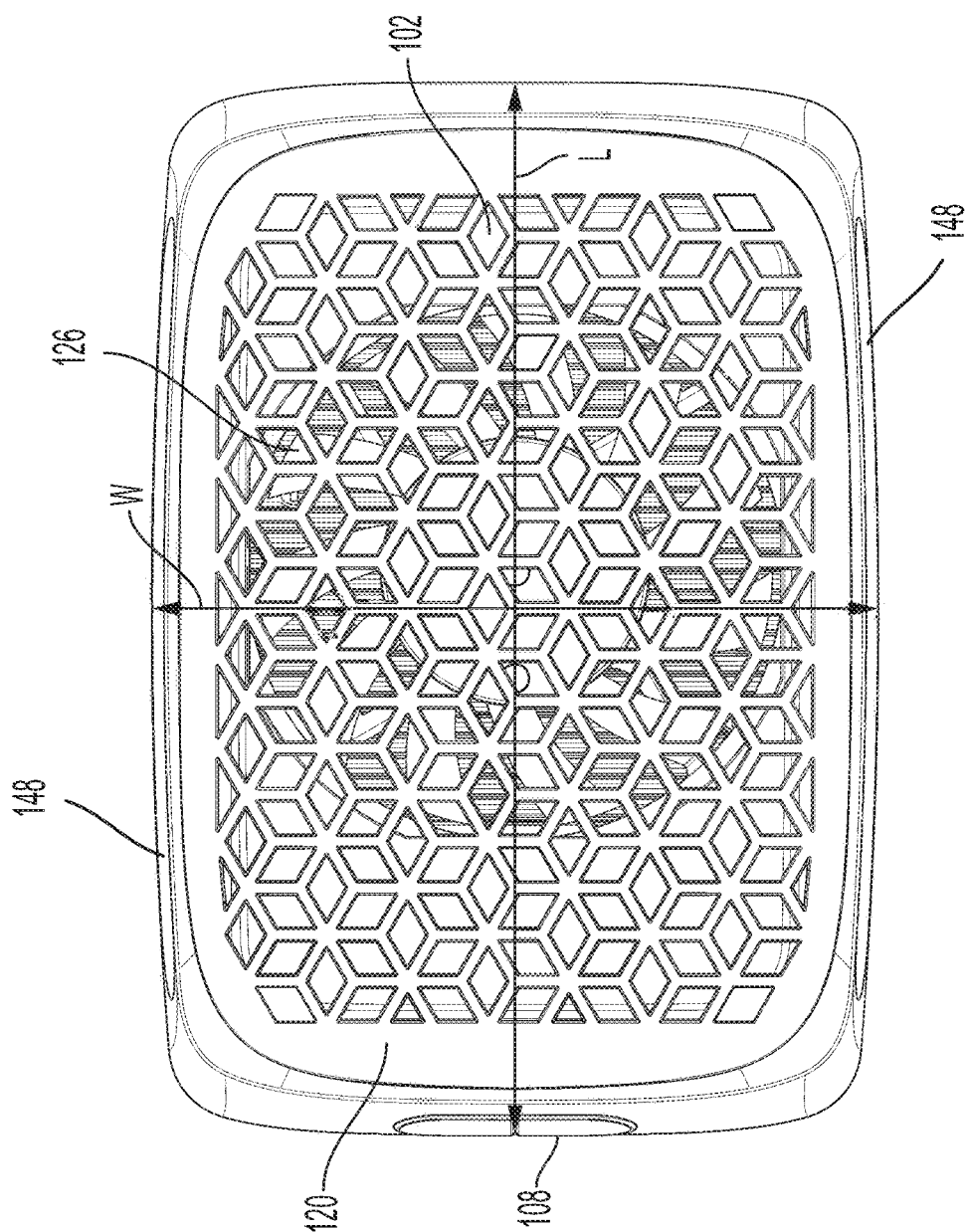
FIG. 4 is a top view of the portable therapeutic temperature-controlled device according to aspects of the present disclosure.

Referring to FIGS. 3 and 4, in some aspects, the temperature-controlled device 10 has a generally cuboid shape with curved surfaces and may have a dimension that a user can easily grasp by one hand. For example, the housing 100 may have a length approximately between 110 mm and 115 mm (L), a width approximately between 75 mm and 80 mm (W), and a height approximately between 52 mm and 58 mm (H). This is one exemplary dimension such that each of length, width, and height may be smaller or greater than what's described herein. The housing 100 may be formed of a plastic material, e.g., one or more bonded layers of one or more of polyester (polyether), polyethylene, polypropylene, nylon, kevlar, nomex, polyacrylonitrile, cellulose, polyurethane, polycarbonate, and acrylonitrile-butadiene-styrene terpolymer, or similar foams and/or fibers. However, it is not limited to the listed materials for the housing 100, but any non-metallic materials, metallic, wood, or the like could be properly implemented. In addition, the housing 100 is curvedly shaped so as to be ergonomic and to facilitate gripping by a user's hand.

To promote proper one-handed gripping, the upper portion of the outer side surfaces has grip portions 148 inwardly curved forming a concave surface to provide comfort grasp particularly for fingers. Such a shape can induce a user to hold the temperature-controlled device 10 in a certain position as shown in FIGS. 11 and 12. The shape and dimensions of housing 100 are configured so as to prevent the buttons 108, the first LEDs 110, the charging port 112, and the second LED 114 from being accidentally gripped or covered when the user is holding the temperature-controlled device 10. Further, the size and dimensions of the air inlet 102 and the air outlet 104 are configured such that they are exposed, partially or entirely, when a user is gripping the temperature-controlled device 10, which facilitates air flow within the housing 100 even when the temperature-controlled device 10 is being held. However, the shape is not limited to what is shown in the drawings or described above. In other words, the temperature-controlled device 10 may have a cylindrical shape, a spherical shape, a hemispheric shape, a prism shape (e.g., triangular prism, hexagonal prism, pentagonal prism, or the like), a cone shape, a tetrahedron shape, an octahedron shape, etc.

The configurations according to various aspects enable the compact size and light weight of the temperature-controlled device 10, as well as efficient and portable power management, which enables a user to engage in an active life-style while still obtaining a thermal therapy. Further, overheating of the temperature-controlled device 10 can be prevented.

Referring back to FIG. 3, the housing 100 may include individually configured parts assembled together, including a top cover 120 having a convex shape, an upper side cover 122, and a lower side cover 124. The top cover 120 forms a top portion of the housing 100, the upper side cover 122 is assembled to the top cover 120, and the lower side cover 124 is then assembled to the upper side cover 122. Each cover may be configured with a curved surface such that the top cover 120, the upper side cover 122, and the lower side cover 124 together form a convex contour of the housing 100 for ergonomic design. In addition, the upper side cover 122 and the lower side cover 124 are assembled forming a partially enclosed space of the housing 100 together with the top cover 120.

The top cover 120 may include a first plurality of vents or openings that form the air inlet 102 to be formed on an upper surface or top surface of the housing 100. The first plurality of vents may be defined on the entire surface, or partially, of the top cover 120. The air inlet 102 may be configured to guide air flow into the housing 100 through the first plurality of vents. For instance, a fan ("126" in FIG. 4) may be located adjacently under the top cover 120 to cause the air flow to flow into the housing 100 through the first plurality of vents. The lower side cover 124 may be formed with a second plurality of vents or openings on the longer (longitudinal) side of the lower side cover 124 of the housing 100 as the air outlet 104 to permit the air flow to flow or exit out from the housing 100, on the shorter (width) side of the lower side cover 124, or a combination of both. Accordingly, the first plurality of vents and the second plurality of vents are configured to define an air flow passage for the air flow in and out of the housing 100. In addition, an air flow passage may be formed from the first plurality of vents as the air inlet 102 and the undercut 116 as a third opening to the second plurality of openings as the air outlet 104 through the fan 126 and the heat sink 132.

Alternatively or additionally, the second plurality of vents or openings may be formed on one side surface, two side surfaces (e.g., opposite side surfaces), three side surfaces, or all four side surfaces of the lower side cover 124. For instance, FIG. 3 shows the air outlet 104 as the second plurality of vents or openings formed on a first surface, while FIGS. 9 and 10 show the air outlet 104 formed on the first surface and a second surface which faces the first surface. In some aspects, the second plurality of vents are arranged longitudinally along the corresponding surface. The plurality of vents or openings of the lower side cover 124 may form the air outlet 104, which may be configured to facilitate the air flow out of the housing 100. In some aspects, the air outlet 104 may be provided on opposite longer (longitudinal) sides or surfaces of the lower side cover 124 (e.g., the first and second side surfaces facing each other) to guide inside air to flow out of the housing 100 in opposing directions. In some aspects, the air outlet 104 is formed on side surfaces of the housing 100 so as to avoid air flowing out from the air outlet 104 does not blow onto a user's skin. In some aspects, the air outlet 104 is positioned on the side surface the housing 100 so as to prevent the user from being able to obstruct air flow while holding the housing 100.

The housing 100 may further include a fan 126 configured to draw or pull outside air into the housing 100. Referring to FIG. 4 which shows a top view of the temperature-controlled device 10, the fan 126 may be located directly, adjacently below the top cover 120 for drawing outside air into the housing 100 through the air inlet 102. The fan 126 is configured to circulate the air inside the housing 100 and guide out, through the air outlet 104, to exit the housing 100.

Referring back to FIG. 3, the pair of recesses 106 that are surface-treated may be formed on opposing side surfaces (e.g., third and fourth surfaces positioned facing each other in a width direction) of the lower side cover 124. In some aspects, the recesses 106 are formed on the sides where the air outlet 104 are not defined. For example, the air outlet 104 may be formed on the longer (longitudinal) side or sides of the lower side cover 124 while the recesses 106 may be formed on the shorter (width) side or sides of the lower side cover 124 as illustrated in FIG. 3. In other aspects, the air outlet 104 and the recesses 106 may be configured on the same side of the lower side cover 124. The recesses 106 may be configured to receive a strap case which will be described below.

In some aspects, the upper side cover 122 may include an undercut 116 configured as a recessed surface positioned along an upper edge of the upper side cover 122 adjacent to the top cover 120. The undercut 116 can form a gap between the top cover 120 and the upper side cover 122 and is configured to facilitate additional and/or alternative air to flow into the housing 100. That is, in some aspects, the undercut 116 may be implemented with the air inlet 102 as a second air inlet such that air is permitted to flow into the housing 100 through the air inlet 102 and additional air through the undercut 116, as shown by the arrows in FIG. 3. In other aspects, the housing 100 may comprise only one of the air inlet 102 and the undercut 116 to receive air.

When a user is grasping the temperature-controlled device 10 by one hand, with reference to FIGS. 11 and 12, the air inlet 102 may be, partially or entirely, blocked and air flow into the housing 100 may be partially obstructed by the user's hand. In any situation, the undercut 116 is configured to provide an additional air passage for additional air to be drawn into the housing 100 to supplement the air flow of the air inlet 102. The air inlet 102, the undercut 116, and the fan 126 are configured to facilitate air flow through a central path within an internal cavity of the housing 100 of the temperature-controlled device 10. For instance, the air inlet 102 together with the undercut 116 and the air outlet 104 are in fluid communication with each other via the central path within the internal cavity (for example, see shaded area "A" in FIG. 7). Maximal air flow in housing 100 can be provided by the combination of the air inlet 102, the undercut 116, and the fan 126, along with the physical arrangement of components within housing 100 within the temperature-controlled device 10. The increased air flow that results from this arrangement allows the temperature-controlled device 10 to operate efficiently (e.g., fast cooling, fast heating) in the heating, cooling, and contrast modes in a portable handheld device.

Figure 5:
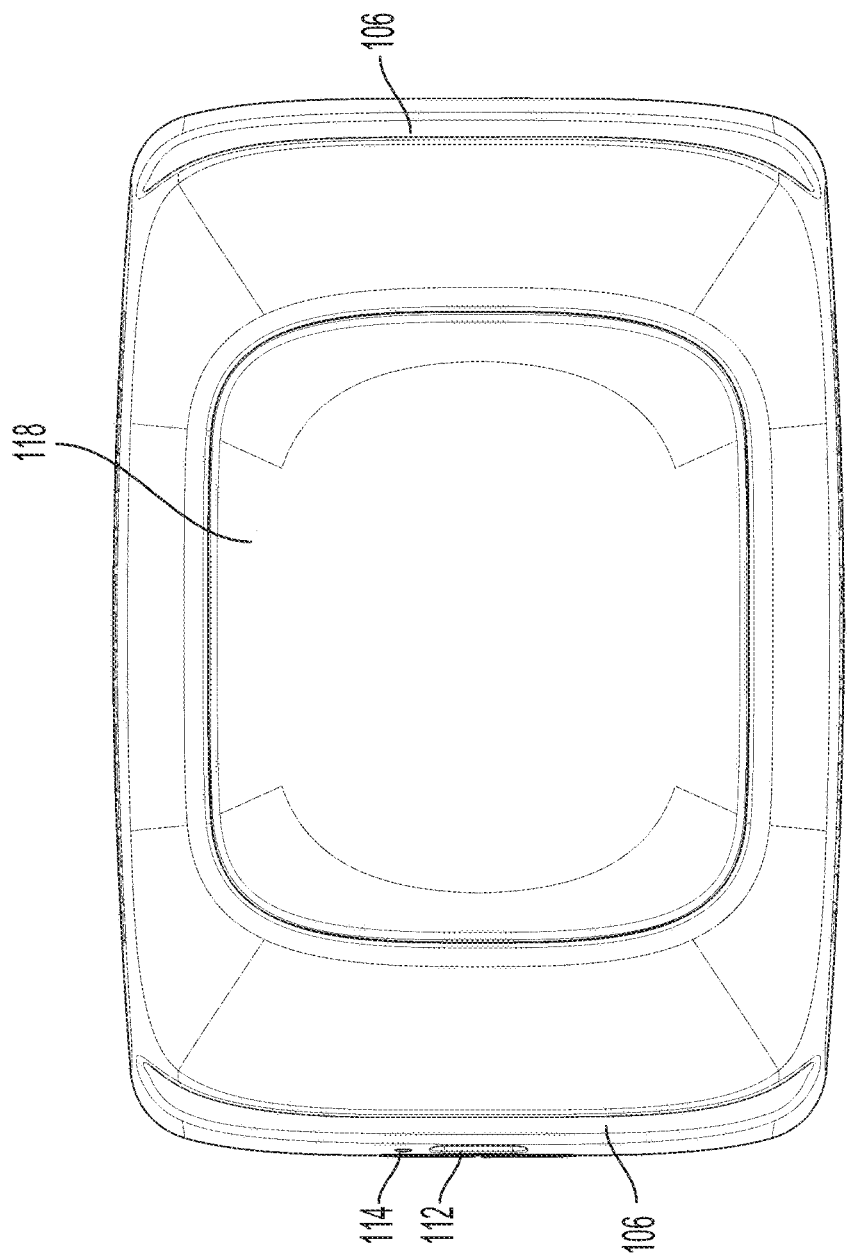
FIG. 5 is a bottom view of the portable therapeutic temperature-controlled device according to aspects of the present disclosure.

Referring to FIG. 5, the bottom portion of the housing 100 has an opening (e.g., "146" in FIGS. 6 and 10), which will be described later, through which the heat spreader 118 extends out of the housing 100. In some aspects, the heat spreader 118 is configured with dimensions to extend outside of the housing 100 and beyond a strap case 20 when it is attached to housing temperature-controlled device 10 (see FIG. 14). The heat spreader 118 may be dimensioned so that it is in contact with a skin surface of the user when the temperature-controlled device 10 is used with or without strap case 20. The heat spreader 118 may have a convex-shaped bottom surface to facilitate contact with surface of the user's body and align with the overall curved shape of the housing 100. With such a convex configuration, the amount of material used for the heat spreader 118 may be reduced while maintaining or improving the heat transfer performance. In addition, the heat spreader 118 may be configured to increase or decrease the temperature of about, e.g., 48° C. in about, e.g., 150 seconds, so as to quickly and efficiently deliver the desired temperature to a user. As will be further described later, the heat spreader 118 is designed for material/weight reduction to satisfy the compactness. In some aspects, the heat spreader 118 may be formed of a conductive alloy, metal, or material, such as aluminum, stainless steel, carbon-fiber, or carbon-carbon materials and/or composites. The dimensions of the spreader 118 may be tailored for the particular application. Such dimensions as well as the shape may be configured to reduce amount of material used while increasing the contact area with a user. For example, curved outer surfaces, rather than flat surfaces, can enhance the contact with the user's body, or unnecessary materials can be removed to reduce the overall size and weight.

Internal components of the temperature-controlled device 10 and their arrangement within housing 100 will be described in detail with reference to FIGS. 6-10.

Figure 6:
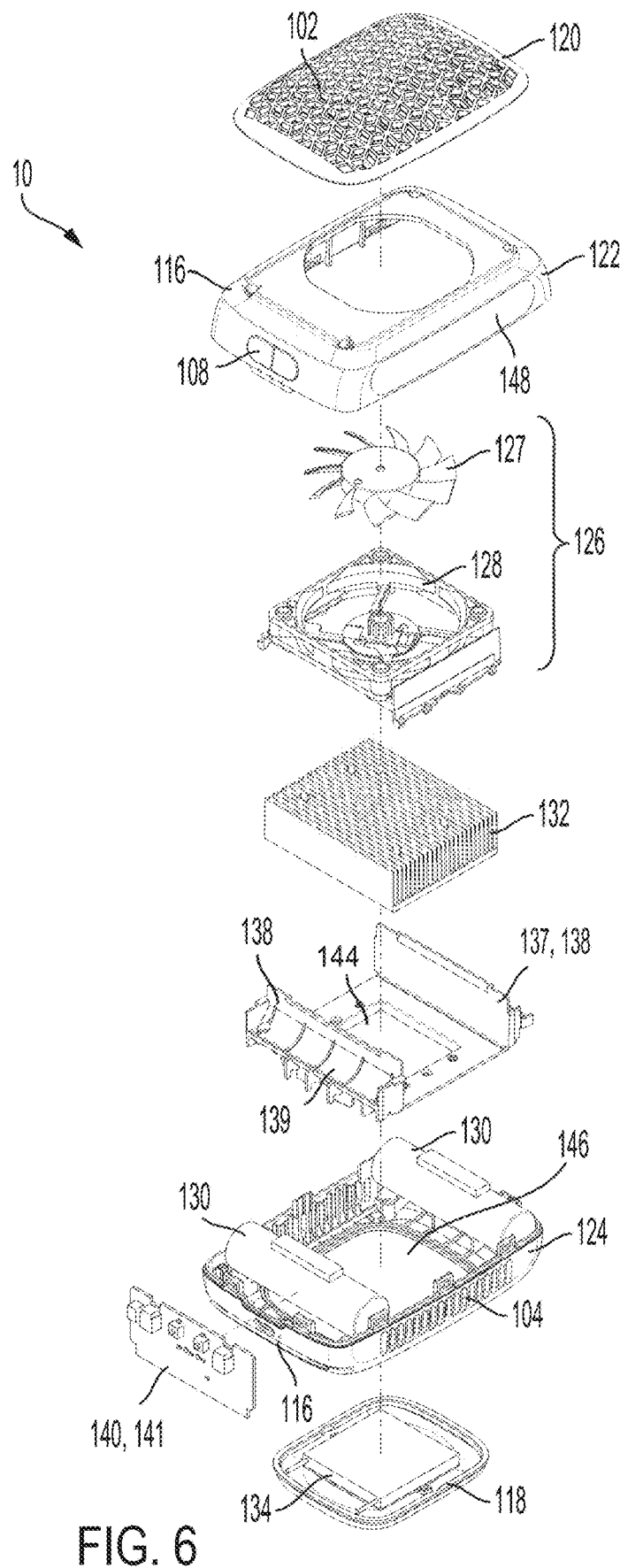
FIG. 6 is an exploded view of the portable therapeutic temperature-controlled device according to aspects of the present disclosure.

FIG. 6 is an exploded view of the temperature-controlled device 10, where each case part of the housing 100 is opened to show internal components of the temperature-controlled device 10 enclosed inside the housing 100. As described above, the temperature-controlled device 10 includes the fan 126 that may be composed of a fan blade portion 127 and a fan housing 128. The fan 126 may be arranged adjacently below the top cover 120 inside the housing 100 to pull ambient air into the housing 100 via the air inlet 102. In some aspects, a heat sink 132 may be arranged beneath the fan 126. The heat sink 132 may be disposed on a first surface of controllable temperature element 134, which can generate cooling and heating. In some aspects, the first surface of controllable temperature element 134 is an upper surface. Examples of the controllable temperature element 134 include a Peltier device, Peltier heat pump, solid state refrigerator, thermoelectric cooler (TEC), etc. The controllable temperature element 134 may adapt the Peltier effect to create a heat flux at the junction of two different types of materials, and transfer heat from one side of the device to the other. In some aspects, a second surface of the controllable temperature element 134 is in contact with a first side (or one side) of the heat spreader 118 so as to transfer thermal energy to the upper surface of the heat spreader 118. In some aspects, the second surface may oppose the first surface; for example, when the first surface is implemented as an upper surface of controllable temperature element 134, the second surface may be implemented as a lower surface of controllable temperature element 134. A second side (or another side) of the heat spreader 118 that opposes the first side of the heat spreader 118 may be disposed inside the housing 100. The first side of the heat spreader 118 may extend out from the housing 100.

The heat sink 132 can pull heat from the upper surface of the controllable temperature element 134, and the fan 126 can help dissipate heat or direct heat away from the heat sink 132 and other components. When the temperature-controlled device 10 is in use, the heat spreader 118 is cooled or heated by the controllable temperature element 134 and the heat or cold can be transferred to, by contacting, a user via the heat spreader 118. In some aspects, the temperature-controlled device 10 further includes a printed circuit board or PCB 140 for electrical and data communication. The PCB 140 may include a control unit (e.g., temperature controller) 142 connected to communicate with the controllable temperature element 134 for various control functions (e.g., turning on or off the temperature-controlled device 10, heating or cooling, etc.).

The controllable temperature element 134 may be implemented as a heat pump that can directly convert electricity into heating and cooling power depending on the mode of the temperature-controlled device 10. When power is supplied to the controllable temperature element 134, the current causes one side (cool side) of the controllable temperature element 134 to absorb heat. The opposite side of the controllable temperature element 134 may then release heat (the hot side). For instance, when a user presses one of buttons 108 for a heating mode, one side of the controllable temperature element 134 releases heat where the one side is in contact with the user. When a user presses one of buttons 108 for a cooling mode, on the other hand, the same side of the controllable temperature element 134 may absorb heat rather than releasing the heat to provide a cooling effect to the user. Further, during a contrast mode, the controllable temperature element 134 may be controlled to periodically alternate heat release and absorption functions. That is, the controllable temperature element 134 causes heat to flow from the cool side to the hot side. Reversing the current causes the heat to be moved in the opposite direction thereby reversing the hot side and the cold side. Consequently, the heating or cooling effect can be selectively performed. Based on the disclosure provided herein, one of ordinary skill in the art will recognize the various possible reconfigurations of temperature-controlled device 10 that would achieve a heating/cooling effect.

The controllable temperature element 134 may have dimensions of approximately, e.g., 40 mm (L)×40 mm (W)×4.8 mm (D), while the heat sink 132 has a surface area slightly greater than the controllable temperature element 134. The fan 126 may have the overall dimensions of approximately, e.g., 60 mm (L)×60 mm (W)×10 mm (D). The heat spreader 118 may have dimensions of approximately, e.g., 70 mm (L)×60 mm (W)×7 mm (D). The disclosed dimensions are however not limited to these numeric values and may be configured within a range of sizes to maintain the ability for one-handed gripping of the temperature-controlled device 10.

Figure 7:
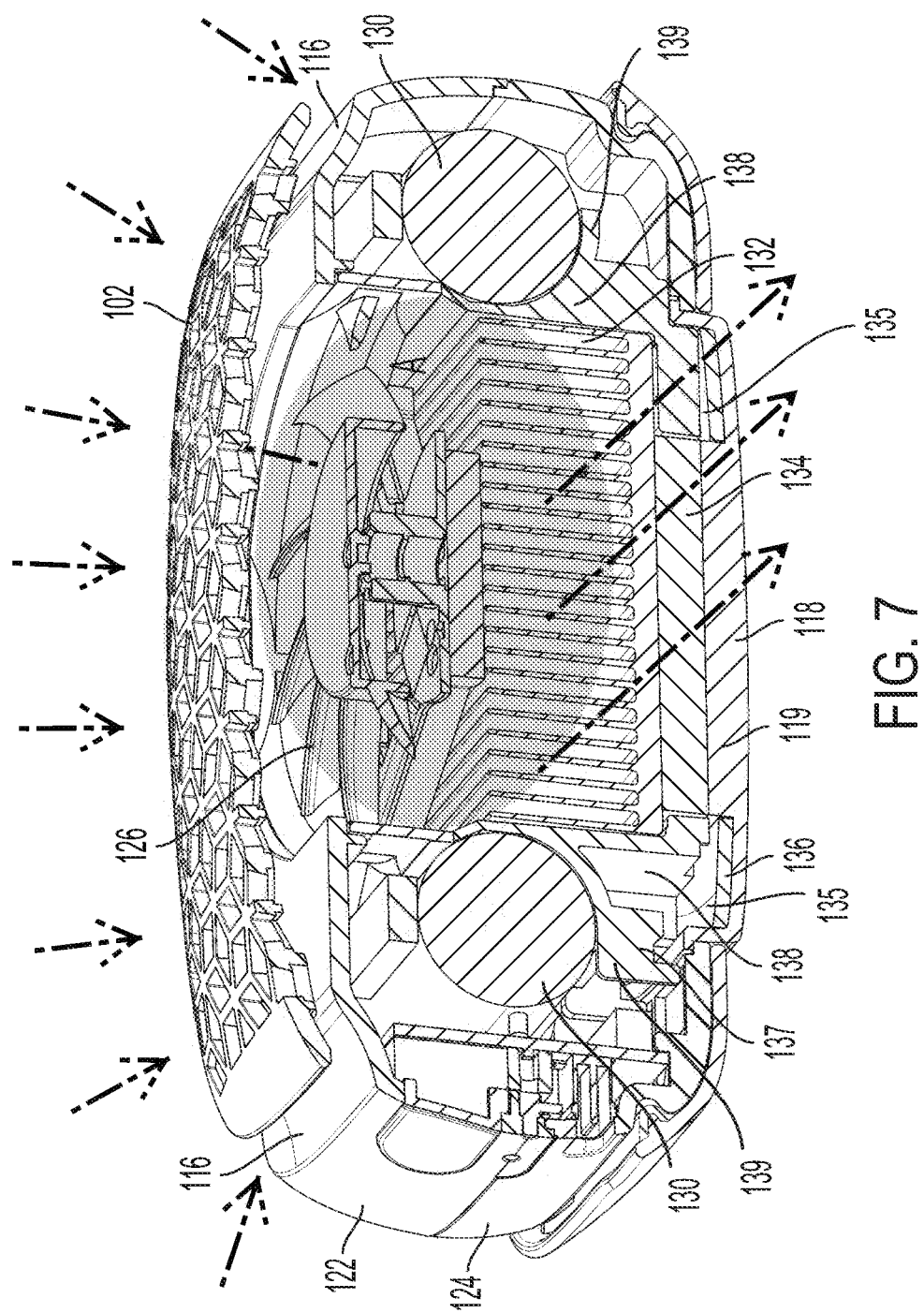
FIGS. 7 and 8 are cross-sectional views of the portable therapeutic temperature-controlled device according to aspects of the present disclosure.
Figure 8:
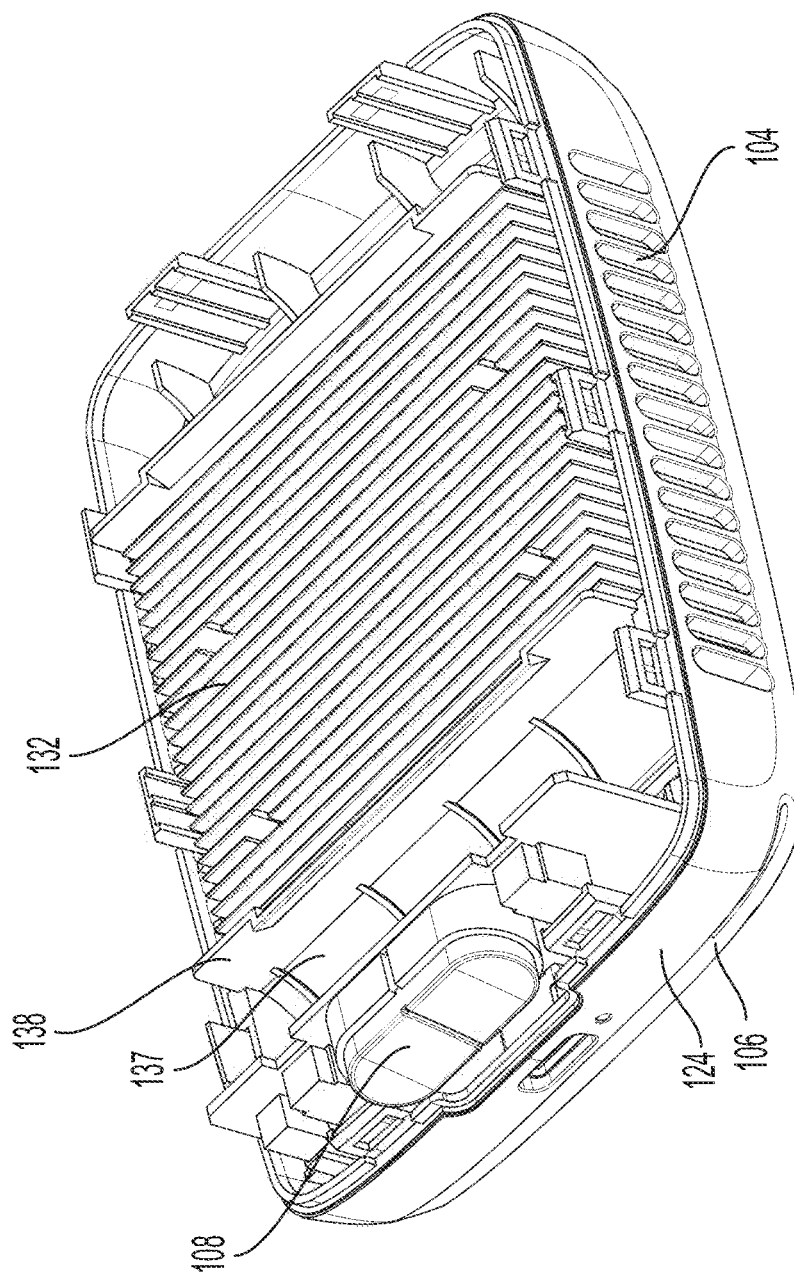

The temperature-controlled device 10 further includes one or more batteries 130 which include at least one battery. In some aspects, the one or more batteries 130 may be one or more rechargeable batteries and may be arranged on one or more sides of the perimeter of the heat sink 132. Referring to FIG. 7, which is a cross-sectional view of FIG. 1, the one or more batteries 130 may include two rechargeable batteries seated on an outer side of a support member 137. The support member 137 may be located inside the housing 100, horizontally off-centered, between the fan 126 and the controllable temperature element 134. The support member 137 may have a square-shaped bottom side on which the heat sink 132 is seated at a middle portion of the support member 137. Two side walls 138 of the support member 137 may extend straightly upward. Each of the two side walls 138 may include a wing portion 139 having a shape for supporting the one or more rechargeable batteries 130 as shown in FIGS. 6-8. In some aspects, one or more side walls of the support member 137 extend as described above to support the corresponding number of rechargeable battery. Accordingly, the support member 137 can support the one or more batteries 130, the heat sink 132, and the fan 126 in a manner that facilitates air flow between the fan 126 to heat spreader 118. Support member 137 is configured to hold the one or more batteries 130 in a horizontally spaced position such that the one or more batteries 130 do not impede air flow within housing 100. In an alternative embodiment, the one or more batteries 130 may be external to the housing 100 and connected to the temperature-controlled device 10 by, for example, a charging cable.

Referring back to FIG. 6, a bottom side of the support member 137 has, at its center, an opening 144 through which the controllable temperature element 134 is fitted to be in contact with the heat sink 132 below the heat sink 132. In addition, the heat spreader 118 may be connected to the bottom side of the support member 137. In some aspects, the opening 144 may be smaller than the heat sink 132 but larger than the controllable temperature element 134. In addition, a padded liner 136 (FIG. 10) having a non-conductive material may be implemented on the second side of the heat spreader 118 inside the housing 100 to protect the controllable temperature element 134 and its surroundings to prevent thermal energy from transferring to unnecessary areas within housing 100, by surrounding the controllable temperature element 134.

The above-described configuration and structure of the internal components can provide a rapid heating and cooling effect to a user through direct contact with the heat spreader 118 while allowing for efficient cooling of the internal components of temperature-controlled device 10. For instance, when a user grasps the temperature-controlled device 10 as shown in FIGS. 11 and 12 for hot or cold therapy, outside air can sufficiently enter the temperature-controlled device 10 through the combination of the air inlet 102 and the undercut 116 by operating the device, and the air can be guided to flow down to the fan 126, the heat sink 132, and finally to outside the housing 100 through the air outlet 104, enabling fast cooling.

In some aspects, the operation (e.g., heating and cooling) of the temperature-controlled device 10 can be controlled by user manipulation of the buttons 108. Referring to FIGS. 7 and 8, the temperature-controlled device 10 may include two or more buttons 108 connected on the PCB 140, where the buttons 108 are on the external surface of the housing 100 for a user to press. The buttons 108 can control turning on and off of the temperature-controlled device 10, changing the control modes, changing temperature settings, etc. Some of the features are controlled by multiple presses of the associated button. In one aspect, one of the buttons 108 may control a heating mode, and the other one of the buttons 108 may control a cooling mode.

More specifically, the buttons 108 may include one button for turning on the temperature-controlled device 10, and the first LEDs 110 may display, e.g., green light, to indicate that the temperature-controlled device 10 is on. The buttons 108 may also include corresponding buttons for activating different modes of the temperature-controlled device 10, such as a button configured to activate (and deactivate) a heating mode and a button configured to activate (and deactivate) a cooling mode. The buttons 108 may be visually distinguishable from each other by icons or colors, e.g., red for heating mode and blue for cooling mode. In addition, two or more buttons of buttons 108 may be configured to be pressed simultaneously to activate a contrast mode. In some aspects, the temperature-controlled device 10 may be configured to detect the length of button presses for the buttons 108. For example, pressing a button for a predetermined period of time (e.g., 2 seconds or less) may cause the temperature-controlled device 10 to switch modes. In some aspects, the predetermined period of time may be different (e.g., shorter or longer) than the period of time needed to press the button for activating a mode or turning on the temperature-controlled device 10.

The heating and cooling modes may be configured with different temperature levels. The heating mode may implement a range of temperature values including predetermined heating thresholds (e.g., above 30° C. but less than 50° C., or alternatively between 35° C. and 43° C.) as a first temperature setting. Examples of discrete values within the range for the heating mode may include, for example, values of 35° C., 39° C., and 43° C. In some other aspects, the temperature range for each mode may vary, such that each range may be greater (e.g., above 20° C. but less than 60° C.) or smaller (e.g., above 38° C. but less than 40° C.).

Similarly, the cooling mode may implement a range of temperate values including a predetermined cooling threshold (e.g., below 20° C., or alternatively between 8° C. and 16° C.) as a second temperature setting. Examples of discrete values within the range for the cooling mode may include, for example, values of 16° C., 12° C., and 8° C. In some aspects, the heating and cooling temperature values of the temperature-controlled device 10 may be specifically chosen to maximize the benefits and safety of treatment directly on users' skin without concern for skin irritation, burns, etc. In some other aspects, the temperature range for each mode may vary, such that each range may be greater (e.g., above 3° C. but less than 30° C.) or smaller (e.g., above 10° C. but less than 18° C.).

The buttons 108 may include one or more buttons for configuring the temperature settings in each mode. In some aspects, the buttons 108 may be configured to activate modes based on a duration of a button press (e.g., a long press for 5 seconds). For example, after activating a desired mode, continuous pressing of the button may result in cycling between different temperature settings until the right temperature setting is selected. The first LEDs 110 may be multi-colored (e.g., bicolor, tricolor) and may indicate the currently selected temperature setting (e.g., a current temperature of the corresponding temperature mode) by displaying each temperature setting in different colors (e.g., blue, orange, red). In some aspects, the first LEDs 110 are configured to display the first temperature setting in the heating mode in a first color, a second LED 114 is configured to display the second temperature setting in the cooling mode in a second color. The first color and the second color may be different colors.

In some aspects, the contrast mode may alternate between the cooling mode and heating mode. The contrast mode may include one or more cycles that alternate between the cooling mode and the heating mode for predetermined time periods. For example, a cooling mode of, e.g., 8° C. may be maintained for a certain period (e.g., 1 min) and then switched to a heating mode of, e.g., of 43° C., for a certain period (e.g., 1 min). The temperature and period settings may be a preset or user configuration settings, e.g., the temperature-controlled device 10 may be configured to communicate with a user device such as a mobile phone or computer. In some aspects, the combination of heating and cooling therapy provided by the temperature-controlled device 10 in contrast mode may be beneficial in helping a user maximize recovery of an area of their body that may be fatigued or sore from activity.

When a desired mode (e.g., cooling, heating, or contrast) is selected by a user, the temperature change can be achieved quickly, e.g., it may take about 2 seconds to drop A 15° C., or it may take about 1 second to increase A 15° C. This is possible due to the above-described structural arrangement of each element forming, e.g., the air flow path from the air inlet 102 and the undercut 116 as a secondary air inlet to the air outlet 104 passing through the internal components within the housing 100.

Below the first LEDs 110, the housing 100 further includes the charging port 112 connected to and electrically communicating with the PCB 140 to charge the one or more rechargeable batteries 130 (see FIG. 1). The second LED 114 may be located adjacent the charging port 112 and display a charging level in different colors. In some aspects, the buttons 108, the first LEDs 110, the charging port 112, and the second LED 114 are on the shorter side (e.g., width direction) of the housing 100 having a generally cuboid shape, while the air outlet 104 are formed on the longer sides (e.g., length direction) of the housing 100. In addition, one among the pair of recesses 106, which will be described later in detail, is formed below the charging port 112 on the same side of the housing 100 without interfering with any of the control/display elements.

In some aspects, although not limited, the one or more rechargeable batteries 130 may be lithium-ion batteries and may have a battery life about 60 minutes. In some aspects, the batteries 130 may be Nickel Cadmium (Ni—Cd), Nickel Metal Hydride (Ni-MH), Lithium Ion (Li-ion), Lithium Polymer (Li—Po), or other type of rechargeable batteries. In some aspects, batteries 130 may be implemented as disposable batteries. The batteries 130 may be in electric communication with the electronic components, e.g., the fan 126, the controllable temperature element 134, and the PCB 140, via one or more electrical contacts. The batteries 130 may be arranged on one or more sides of the perimeter of the fan 126, the heat sink 132, and the controllable temperature element 134, so as not to interfere with the air flow and thermal transfer through a central path of the internal cavity of the temperature-controlled device 10 (refer to the arrows in FIG. 19). Further and as also described above, the batteries 130 are horizontally spaced apart from each other by the fan 126, the heat sink 132, and the controllable temperature element 134 as well as any internal electronic components so as to form a path within housing 100 through which air may flow.

For example, as shown in FIG. 7, when the temperature-controlled device 10 includes two batteries 130 supported on the support member 137 adjacent the third and fourth surfaces of the lower side cover 124. That is, each battery 130 is seated on the corresponding wing portion 139 located at each outer side of the support member 137. The wing portions 139 are spaced apart from each other such that internal electronic components, such as the fan 126 and the heat sink 132 can be positioned in the space between the wing portions 139 (or the two side walls 138). As described above, such a configuration guides air flow through a path formed within the housing 100 to cool internal components in proximity to the path. This air path formed between the batteries 130 can facilitate air to quickly cool the internal components, etc.

FIGS. 9 and 10 show an internal view and an exploded view of the lower side cover 124, respectively. The lower side cover 124 has a first opening 145, through which the buttons 108, the first LED 110, the charging port 112, and/or the second LED 114 are exposed, on a surface (e.g., third side surface) of the housing 100. The housing 100 further includes a second opening 146 on a bottom surface facing the top surface of the temperature-controlled device 10 such that the heat spreader 118 extends out through the second opening 146. In some aspects, the first and second side surfaces of the housing 100 extending in the length direction may be longer than the third side surface extending in the width direction. As described above, the heat spreader 118 may have a recessed portion 135 to securely receive the controllable temperature element 134. The recessed portion 135 may reduce the weight/cost of the temperature-controlled device 10 by reducing or minimizing the use of unnecessary material.

For instance, referring back to FIG. 7, rather than having a flat surface in a solid body shape, the heat spreader 118 has the recessed portion 135 recessed on the top such that a center portion 119 is configured to protrude from the recessed portion 135 to contact the controllable temperature element 134. The controllable temperature element 134 further includes a padded liner 136 to surround the heat spreader 118 preventing thermal energy from transferring from or to the heat spreader 118 in addition to protecting the heat spreader 118.

FIGS. 11 and 12 illustrate the portable therapeutic temperature-controlled device 10 grasped by a user's hand in various views. In particular, FIG. 12 illustrates that air flow from the air inlet 102 to the air outlet 104 is assured (e.g., the arrows).

Figure 13:
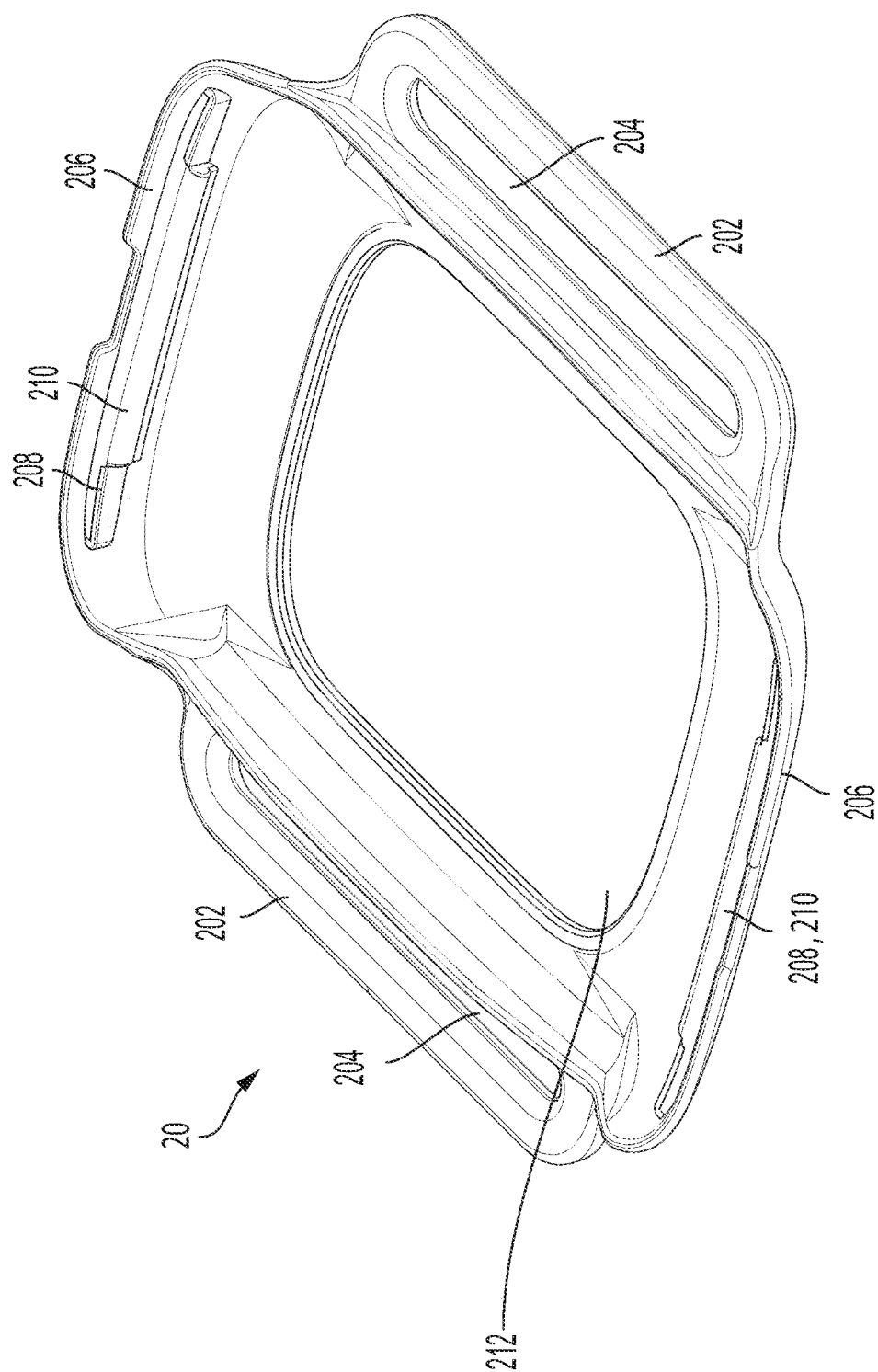
FIG. 13 is a perspective view of a strap case according to aspects of the present disclosure.
Figure 14:
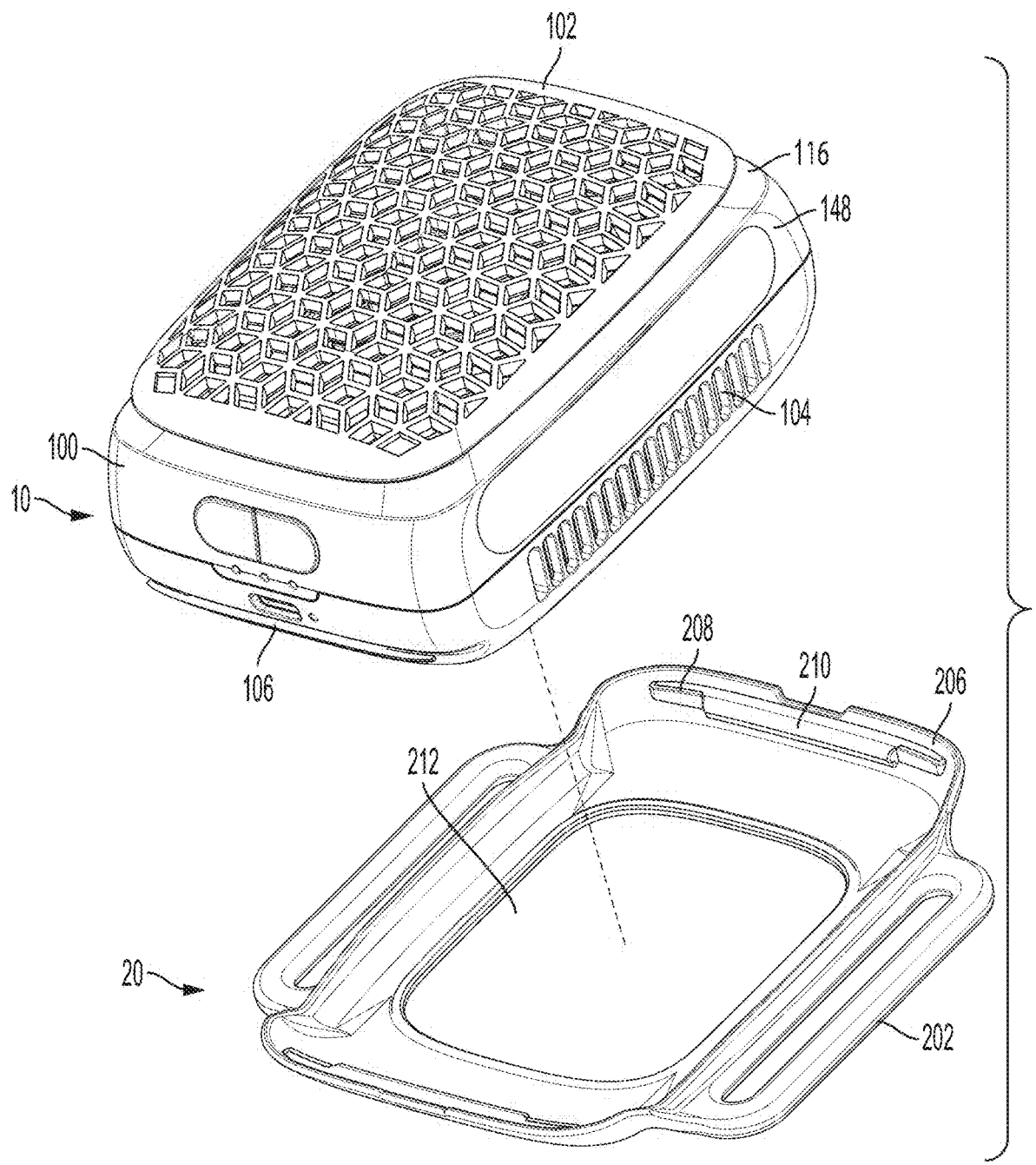
FIG. 14 is a perspective view of the strap case of FIG. 13 and the portable therapeutic temperature-controlled device of FIG. 1.

FIGS. 13 and 14 show a strap case 20 that is designed to receive the temperature-controlled device 10. The strap case 20 is generally formed of a plastic material similar to the housing 100 and has a rectangular shape. In some aspects, the strap case 20 includes a pair of strap buckle portions 202 at opposite sides each having a buckle opening 204, and a pair of side arms 206 curvedly extending upward. Each side arm 206 has a protrusion 208 extending toward a center opening 212 to snap-fit to the respective recess 106 of the housing 100. In addition, the pair of strap buckle portions 202 may integrally extend away from the center opening 212 in a width direction. Accordingly, the strap case 20 can receive the temperature-controlled device 10 by engaging the protrusion 208 with the respective recess 106. Each protrusion 208 on the pair of side arms 206 is provided with a padded layer 210 thereon to protect the friction between the protrusion 208 and the recess 106. The padded layer 210 may be formed of a silicone material (including thermoplastic silicone, thermoset silicone, and silicone gels) or a rubber material for preventing wear and scratch between the protrusion 208 with the respective recess 106 when assembling and disassembling. In some other aspects, a plastic material may be used for the padded layer 210 using rough textures thereon.

Figure 15:
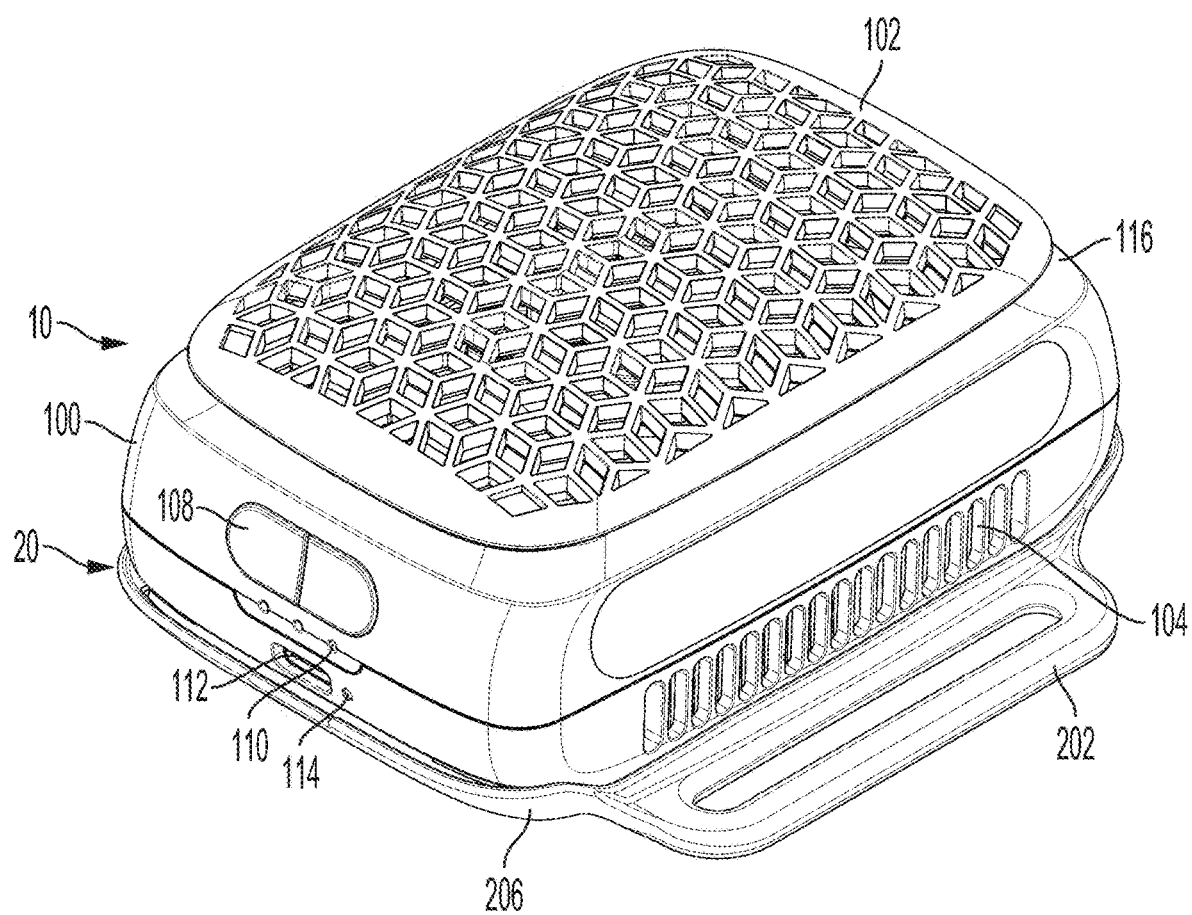
FIG. 15 is a perspective view of the strap case and the portable therapeutic temperature-controlled device as assembled.
Figure 16:
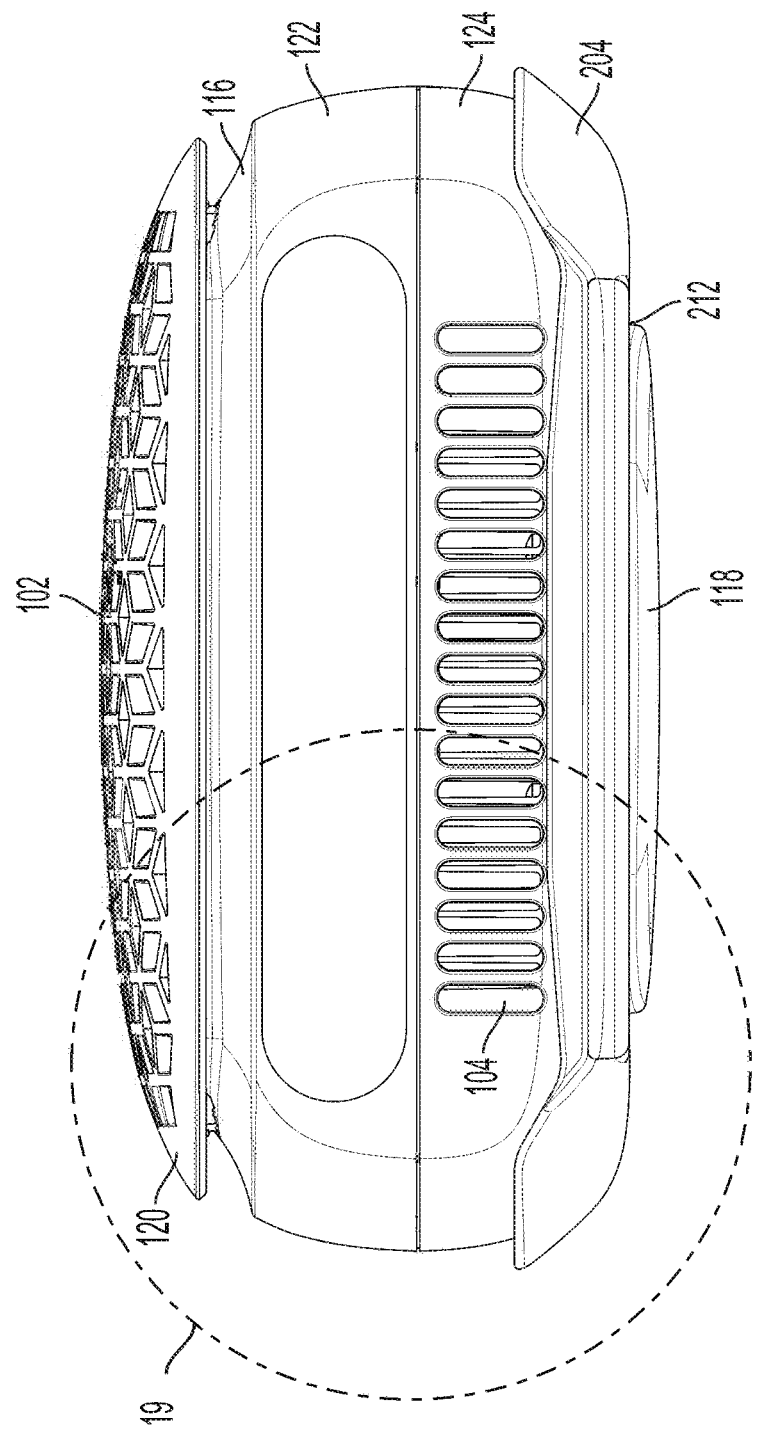
FIG. 16 is a side view of the strap case and the portable therapeutic temperature-controlled device as assembled.
Figure 17:
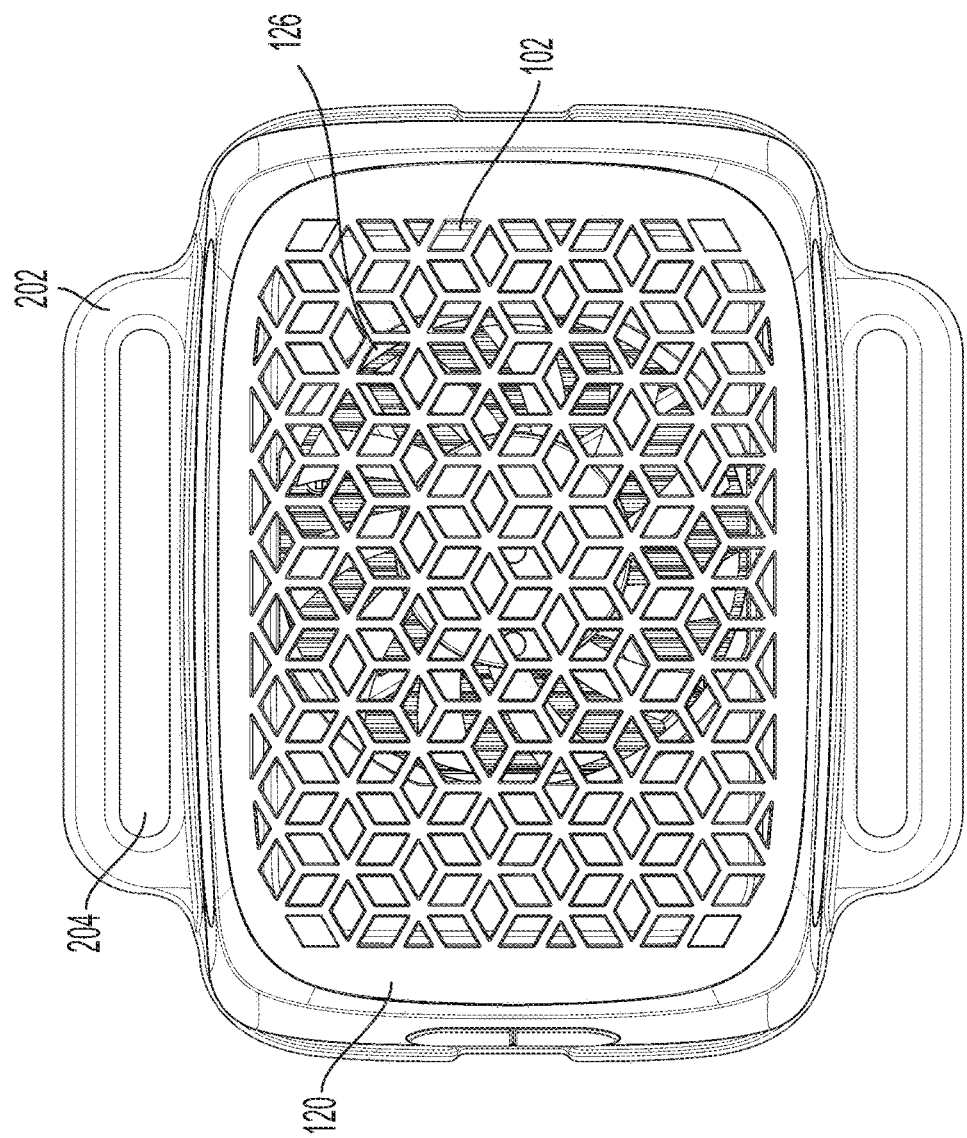
FIG. 17 is a top view of the strap case and the portable therapeutic temperature-controlled device as assembled.
Figure 18:
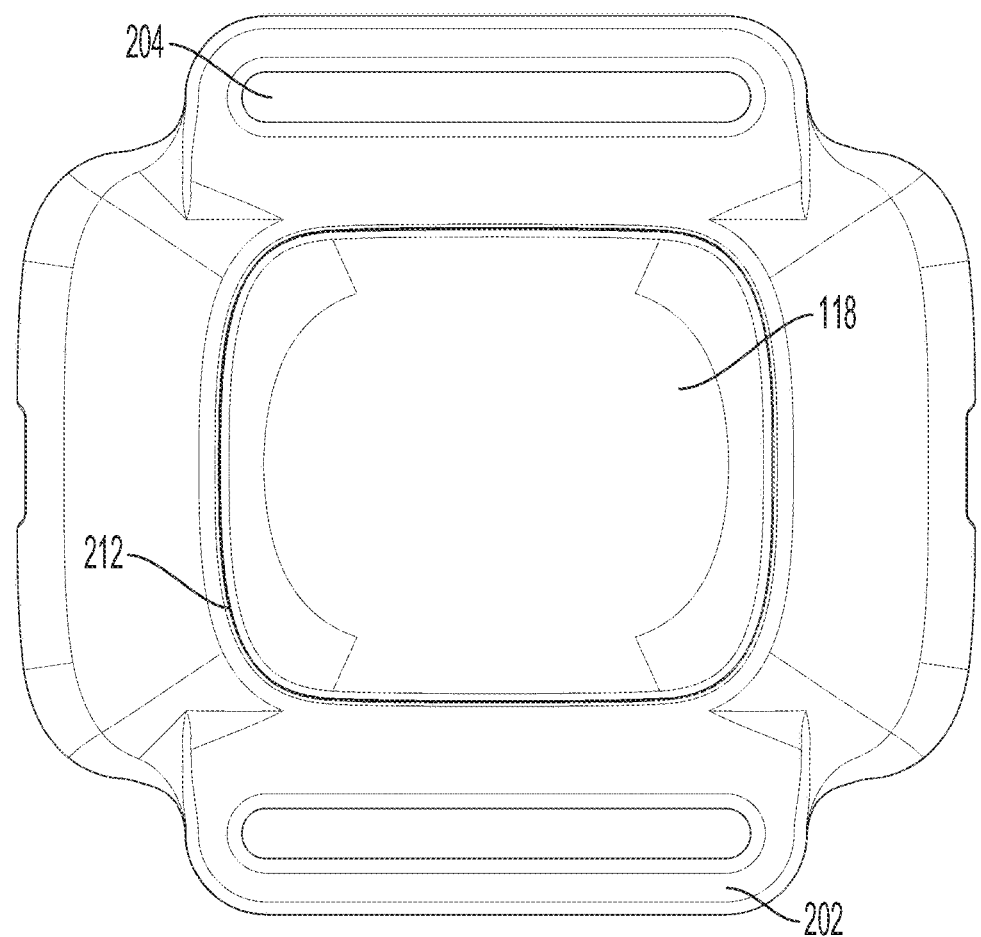
FIG. 18 is a bottom view of the strap case and the portable therapeutic temperature-controlled device as assembled.

FIGS. 15-19 show an assembly of the strap case 20 and the temperature-controlled device 10 in various views. As shown in FIG. 15, when the strap case 20 and the temperature-controlled device 10 are assembled, the air inlet 102 and the air outlet 104 are fully exposed. In addition, referring to FIG. 16 as well as FIG. 14, the heat spreader 118 extends on a bottom side of the strap case 20 through the center opening 212 of the strap case 20 to assure the first contact to a user's body. FIG. 17 shows a top view of the assembly of the strap case 20 and the temperature-controlled device 10, and FIG. 18 shows a bottom view of the assembly. As shown, the top cover 120 includes a plurality of openings forming the air inlet 102 allowing air to enter by the help of the fan 126.

Figure 19:
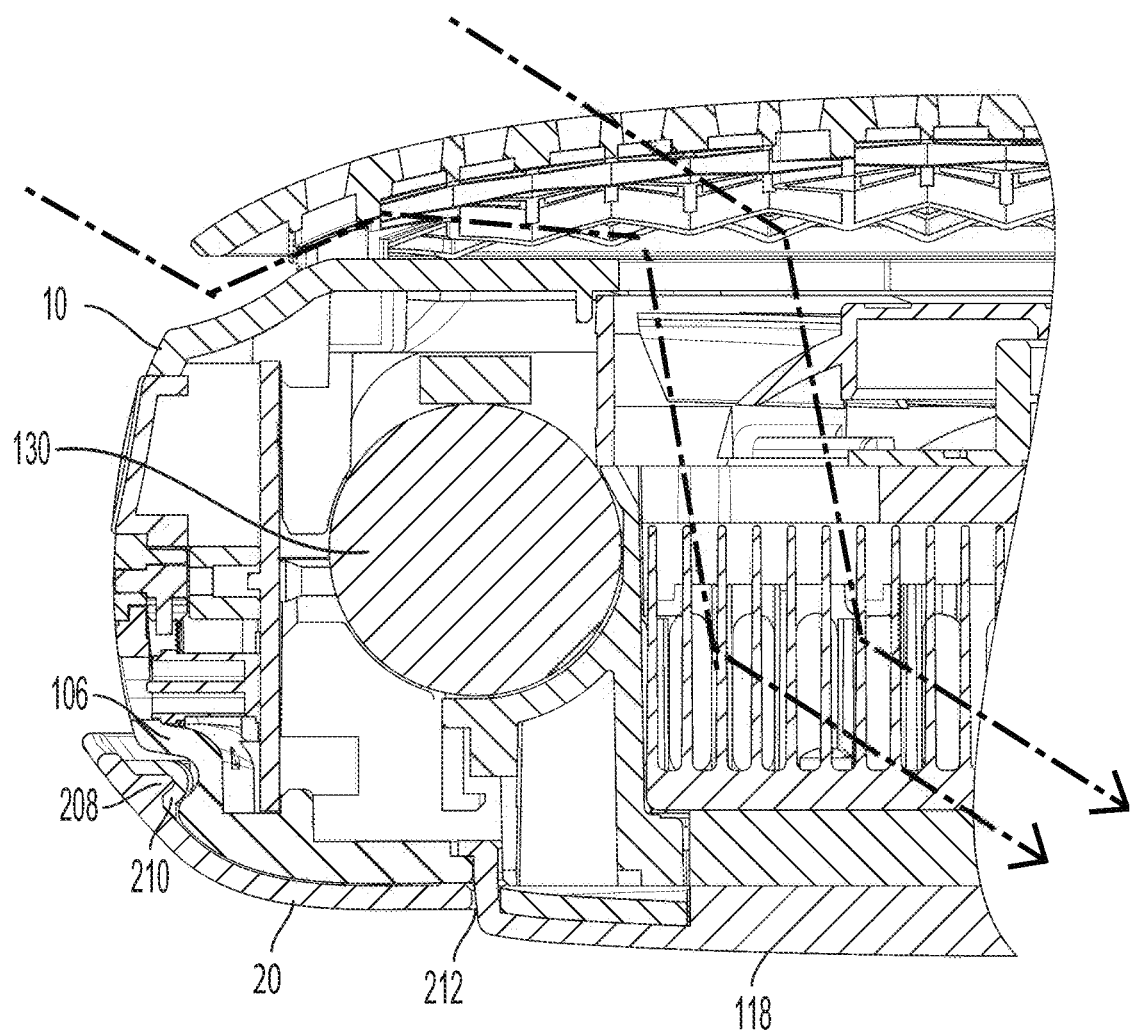
FIG. 19 illustrates a magnified cross-section view of FIG. 16.

FIG. 19 is a magnified cross-sectional view of FIG. 16 where the strap case 20 and the temperature-controlled device 10 are snap-fitted by the respective protrusion 208 and the recess 106, with the padded layer 210 protecting the contact portion as well as securing the connection between the strap case 20 and the temperature-controlled device 10. In addition, the battery 130 may be horizontally spaced apart from any internal electronic and metallic components of the temperature-controlled device 10. This arrangement allows air flow (the arrows in FIG. 19) to enter the temperature-controlled device 10 and exiting the temperature-controlled device 10 without being blocked by the battery 130, as also described above.

FIGS. 20A, 20B, 21A, 21B, 22A, 22B, 23A, and 23B illustrate a strap system for the assembly of the temperature-controlled device 10 and the strap case 20.

Figure 20A:
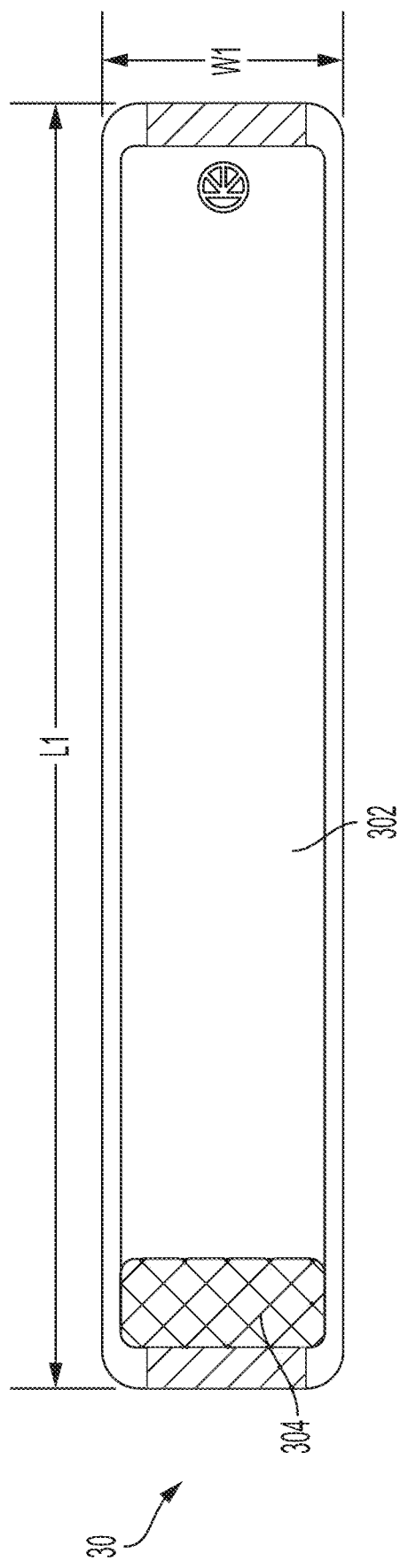
FIGS. 20A and 20B are top and bottom views of a primary strap according to aspects of the present disclosure.
Figure 20B:
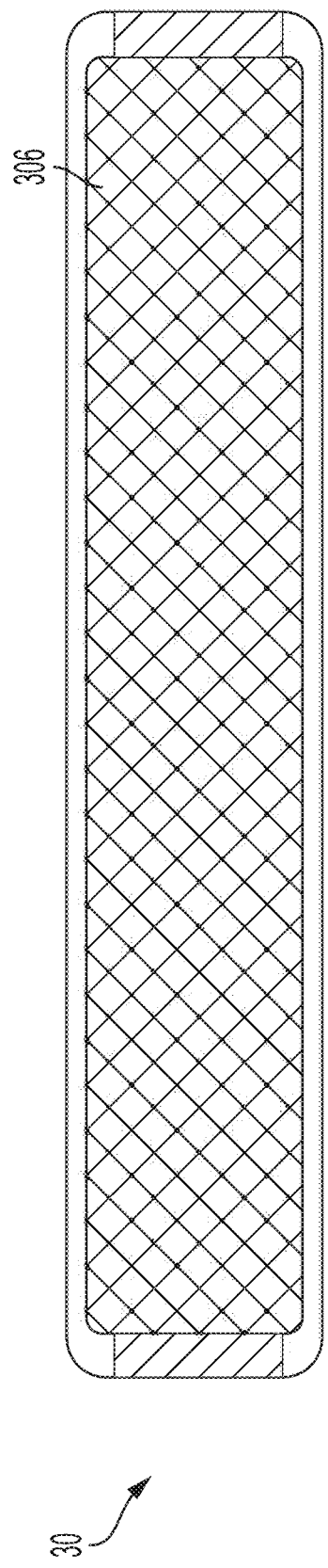

Referring to FIGS. 20A and 20B, the strap system includes a primary strap 30 having a neoprene material 302 on one side or a first side (FIG. 20A) along the entire length and a first hook and loop material 306 (e.g., Velcro) on the entire length of the opposite side or a second side (FIG. 20B). On the neoprene material 302, a second hook and loop material 304 may be partially provided at one end. The primary strap 30 has a first length approximately, e.g., 100 cm (L1) and a first width approximately, e.g., 6 cm (W1), and can be fit through the buckle openings 204 of the strap buckle portions 202. For instance, each end of the primary strap 30 can be inserted through the buckle opening 204 and folded over such that the first hook and loop material 306 can be fastened to each other, as shown in FIGS. 21A and 21B. When the temperature-controlled device 10, the strap case 20, and the primary strap 30 are assembled together, the assembly is configured to strap on a user such that heating and cooling of the controllable temperature element 134 are selectively transferred to the user's body part that is in contact with the heat spreader 118.

Figure 22A:
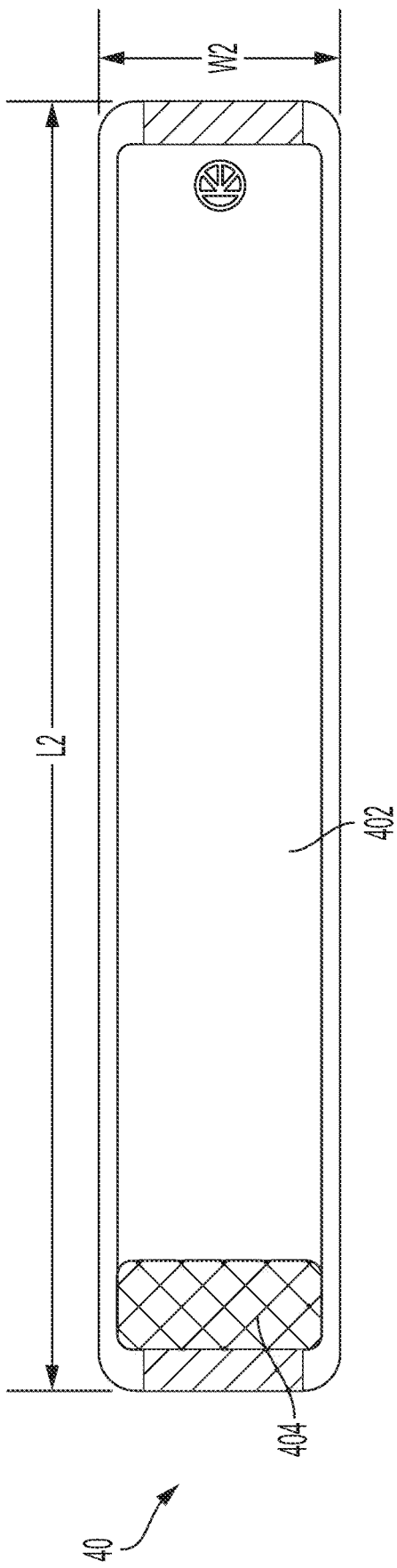
FIGS. 22A and 22B are top and bottom views of a secondary strap according to aspects of the present disclosure.
Figure 22B:
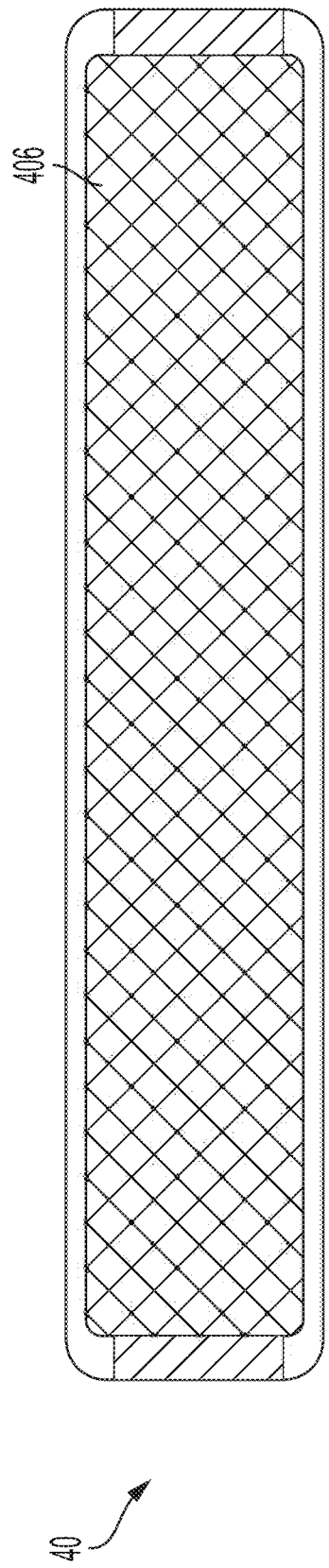

Additionally, with reference to FIGS. 22A and 22B, the strap system includes a secondary strap 40 having a shorter length, e.g., a second length approximately 60 cm (L2) and a second width approximately 6 cm (W2). The secondary strap 40 can be connected to the primary strap 30 to form one long strap system as shown in FIGS. 23A and 23B. Similar to the primary strap 30, the secondary strap 40 may include a neoprene material 402 on a first side of the secondary strap 40 and a third hook and loop material 406 on the entire length of the opposite side. On the neoprene material 402, a fourth hook and loop material 404 is partially provided at one end. The secondary strap 40 can be fit through the buckle openings 204 of the strap buckle portions 202. For instance, each end of the secondary strap 40 can be fit through the buckle opening 204 and folded over such that the third hook and loop material 406 can be fastened to each other. The dimensions of the primary and secondary straps 30, 40 described herein are merely exemplary values and thus not limited thereto.

Alternatively, the secondary strap 40 can be coupled to the one end of the primary strap 30 by fastening the second hook and loop material 304 as a first fastening mechanism and the third hook and loop material 406 as a second fastening mechanism. That is, the adjustable strap system, using the primary strap 30 or secondary strap 40 individually, or together, allows versatile use. For instance, for use on a person with a bigger figure vs. a smaller figure, or strap around the shoulder or back vs. strap around a wrist or ankle, etc.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Aspects using the singular or plural number may also include the plural or singular number respectively. The word "or" in reference to a list of two or more items, covers all of the following interpretations of the word: any of the items in the list, all of the items in the list, and any combination of the items in the list.

The above-detailed description of aspects of the disclosure is not intended to be exhaustive or to limit the teachings to the precise form disclosed above. While specific aspects of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another aspect, instructions or sub-operations of distinct operations may be implemented in an intermittent and/or alternating manner.

The teachings of the disclosure provided herein can be applied to other systems, not necessarily the system described above. The elements and acts of the various aspects described above can be combined to provide further aspects. Any measurements or dimensions described or used herein are merely exemplary and not a limitation on the present disclosure. Other measurements or dimensions are within the scope of the disclosure.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further aspects of the disclosure.

These and other changes can be made to the disclosure in light of the above Detailed Description of the Aspects. While the above description describes certain aspects of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific aspects disclosed in the specification unless the above Detailed Description of the Aspects section explicitly defines such terms. Accordingly, the actual scope of the disclosure encompasses not only the disclosed aspects, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, 9 ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary aspects of the disclosure have been shown and described, it is to be understood that all the terms used herein are descriptive rather than limiting, and that many changes, modifications, and substitutions may be made by one having ordinary skill in the art without departing from the spirit and scope of the disclosure.

What is claimed is:

1. A portable temperature-controlled device comprising:
a housing comprising an upper cover and a lower cover, and configured to enclose:
a controllable temperature element configured to generate cooling and heating;
a heat sink disposed adjacent to the controllable temperature element;
a fan disposed adjacent to the heat sink and configured to direct heat away from the heat sink, wherein the fan is configured to draw outside air into the housing;
a heat spreader comprising a first side and a second side, which is opposite to the first side and in contact with the controllable temperature element, wherein the first side is configured to contact a user's body part while the second side is disposed inside the housing;
at least one battery, wherein the at least one battery, the heat sink, and the fan are disposed inside the housing;
a temperature controller adjacent the at least one battery and connected to the controllable temperature element inside the housing; and
a Printed Circuit Board (PCB) configured for electrical and data communication with the temperature controller, wherein the PCB comprises:
a plurality of buttons for selectively controlling a heating mode and a cooling mode of a temperature mode by user manipulation, wherein the plurality of buttons are further configured for turning on and off the portable temperature-controlled device, wherein the heating mode includes a first temperature setting and the cooling mode includes a second temperature setting; and
a first Light-Emitting Diode (LED) configured to indicate the temperature mode;
wherein the housing comprises a first air inlet configured to permit air flow into the housing through the upper cover and an air outlet configured to permit the air flow to flow out of the housing through the lower cover, and
wherein the first air inlet and the air outlet are in fluid communication with each other.

2. The portable temperature-controlled device of claim 1, wherein the plurality of buttons and the first LED are exposed on a surface of the housing.

3. The portable temperature-controlled device of claim 2, wherein the first temperature setting includes a temperature range between 35° C. and 43° C., and a second temperature setting includes a temperature range between 8° C. and 16° C., and
wherein the first LED includes a plurality of LEDs configured to display different colors from each other, and the plurality of LEDs are configured to indicate a current temperature of the temperature mode.

4. The portable temperature-controlled device of claim 2, wherein the first air inlet is defined on a top surface of the portable temperature-controlled device, wherein the first air inlet is configured to allow the air flow into the housing,
wherein the air outlet is defined on at least one of a first or second side surface of the portable temperature-controlled device, wherein the air outlet is configured to allow the air flow to exit the housing, and
wherein the housing further comprises a first opening on a third side surface and a second opening on a bottom surface facing the top surface of the portable temperature-controlled device.

5. The portable temperature-controlled device of claim 4, wherein the PCB further includes a charging port disposed below the first LED and exposed outside the housing through the first opening of the housing, the charging port electrically communicating with the PCB,
wherein the heat spreader is configured to extend out through the second opening,
wherein the PCB includes a second LED configured to indicate a charging level in different colors, and
wherein the second LED is disposed adjacent the charging port.

6. The portable temperature-controlled device of claim 1,
wherein the housing further comprises a support member, wherein the at least one battery is horizontally spaced apart from the fan and the heat sink and supported on the support member, wherein the at least one battery is positioned so as to permit air flow between the fan and the heat spreader,
wherein the support member has an opening in a center, the opening being smaller than the heat sink but larger than the controllable temperature element, and
wherein the heat spreader is connected to a bottom side of the support member.

7. The portable temperature-controlled device of claim 1, wherein the housing further comprises a middle cover,
wherein the upper cover has a convex shape and is configured to be assembled to the middle cover having an undercut, wherein the undercut is positioned along an upper edge of the middle cover adjacent the upper cover, and wherein the undercut further defines a second air inlet configured to permit additional air flow to enter the housing between the upper cover and the middle cover, and
wherein the middle cover and the lower cover are assembled forming a partially enclosed space of the housing together with the upper cover.

8. The portable temperature-controlled device of claim 7, wherein the upper cover comprises a first plurality of vents, wherein the fan is configured to cause the air flow to flow into the housing through the first plurality of vents, and
wherein the lower cover includes:
a second plurality of vents configured to permit the air flow to exit out from the housing, wherein the second plurality of vents are defined on first and second surfaces of the lower cover arranged longitudinally, and wherein the first and second surfaces are positioned facing each other; and
a pair of recesses defined on third and fourth surfaces, wherein the third and fourth surfaces are positioned facing each other in a width direction.

9. The portable temperature-controlled device of claim 8, wherein the at least one battery is spaced apart from the fan, the heat sink, and the controllable temperature element,
wherein the at least one battery includes two batteries adjacent to the third and fourth surfaces, and
wherein the first plurality of vents, the fan, the heat sink, and the second plurality of vents are arranged to define an air flow passage for the air flow from the first plurality of vents to the second plurality of vents through the fan and the heat sink.

10. The portable temperature-controlled device of claim 1, wherein the second side of the heat spreader is disposed inside the housing and includes a padded liner that surrounds the controllable temperature element, and
wherein the heat spreader is configured to receive thermal energy from the controllable temperature element.

11. A portable temperature-controlled device comprising:
a housing comprising an upper cover, a lower cover, and a support member, wherein the housing is configured to enclose:
   a controllable temperature element configured to generate cooling and heating;
   a heat sink disposed adjacent to the controllable temperature element;
   a fan disposed adjacent to the heat sink and configured to direct heat away from the heat sink, wherein the fan is configured to draw outside air into the housing;
   a heat spreader connected to a bottom side of the support member, the heat spreader comprising a first side and a second side, which is opposite to the first side and in contact with the controllable temperature element, wherein the first side is configured to contact a user's body part while the second side is disposed inside the housing;
   at least one battery supported on the support member and horizontally spaced apart from the fan and the heat sink, wherein the at least one battery, the heat sink, and the fan are disposed inside the housing, and wherein the at least one battery is positioned so as to permit air flow between the fan and the heat spreader; and
   a temperature controller adjacent the at least one battery and connected to the controllable temperature element inside the housing,
wherein the housing comprises a first air inlet configured to permit air flow into the housing through the upper cover and an air outlet configured to permit the air flow to flow out of the housing through the lower cover,
wherein the first air inlet and the air outlet are in fluid communication with each other, and
wherein the support member has an opening in a center, the opening being smaller than the heat sink but larger than the controllable temperature element.

12. A portable temperature-controlled device comprising:
a housing comprising:
   an upper cover having a convex shape;
   a middle cover having an undercut positioned along an upper edge of the middle cover adjacent the upper cover;
   a lower cover, wherein the middle cover and the lower cover are assembled to form a partially enclosed space of the housing together with the upper cover;
   a first air inlet configured to permit air flow into the housing through the upper cover; and
   an air outlet in fluid communication with the first air inlet, the air outlet configured to permit the air flow to flow out of the housing through the lower cover, wherein the housing is configured to enclose:
      a controllable temperature element configured to generate cooling and heating;
      a heat sink disposed adjacent to the controllable temperature element;
      a fan disposed adjacent to the heat sink and configured to direct heat away from the heat sink, wherein the fan is configured to draw outside air into the housing;
      a heat spreader comprising a first side and a second side, which is opposite to the first side and in contact with the controllable temperature element, wherein the first side is configured to contact a user's body part while the second side is disposed inside the housing;
      at least one battery, wherein the at least one battery, the heat sink, and the fan are disposed inside the housing; and
      a temperature controller adjacent the at least one battery and connected to the controllable temperature element inside the housing.

13. The portable temperature-controlled device of claim 12, wherein the undercut further defines a second air inlet configured to permit additional air flow to enter the housing between the upper cover and the middle cover.

14. The portable temperature-controlled device of claim 13, wherein the fan is configured to cause the air to flow into the housing through a first plurality of vents, and wherein the lower cover includes:
   first and second surfaces positioned facing each other in a longitudinal direction;
   a second plurality of vents defined on the first and second surfaces and configured to permit the air flow to exit from the housing;
   third and fourth surfaces positioned facing each other in a width direction; and
   a pair of recesses defined on the third and fourth surfaces.

15. The portable temperature-controlled device of claim 14, wherein the at least one battery is spaced apart from the fan, the heat sink, and the controllable temperature element,
wherein the at least one battery includes two batteries adjacent to the third and fourth surfaces, and
wherein the first plurality of vents, the fan, the heat sink, and the second plurality of vents are arranged to define an air flow passage for the air flow from the first plurality of vents to the second plurality of vents through the fan and the heat sink.

16. A portable temperature-controlled device comprising:
a housing comprising an upper cover and a lower cover, and configured to enclose:
   a controllable temperature element configured to generate cooling and heating;
   a heat sink disposed adjacent to the controllable temperature element;
   a fan disposed adjacent to the heat sink and configured to direct heat away from the heat sink, wherein the fan is configured to draw outside air into the housing;
   a heat spreader configured to receive thermal energy from the controllable temperature element, the heat spreader comprising a first side and a second side, which is opposite to the first side and in contact with the controllable temperature element, wherein the first side is configured to contact a user's body part while the second side is disposed inside the housing, wherein the heat spreader includes a padded liner that surrounds the controllable temperature element;
   at least one battery, wherein the at least one battery, the heat sink, and the fan are disposed inside the housing; and
   a temperature controller adjacent the at least one battery and connected to the controllable temperature element inside the housing, wherein the housing comprises a first air inlet configured to permit air flow into the housing through the upper cover and an air outlet configured to permit the air flow to flow out of the housing through the lower cover, and wherein the first air inlet and the air outlet are in fluid communication with each other.

\* \* \* \* \*